(12) United States Patent
Rowland et al.

(10) Patent No.: US 8,493,187 B2
(45) Date of Patent: **\*Jul. 23, 2013**

(54) WIRELESS SENSOR READER

(75) Inventors: Harry D. Rowland, East Peoria, IL (US); Roger Dwight Walking, Dunlap, IL (US); Balamurugan Sundaram, Peoria, IL (US); Bryan Paul, Peoria, IL (US); In Soo Ahn, Peoria, IL (US); Michael Nagy, Lawrenceville, GA (US)

(73) Assignee: Endotronix, Inc., East Peoria, IL (US)

( * ) Notice: Subject to any disclaimer, the term of this patent is extended or adjusted under 35 U.S.C. 154(b) by 766 days.

This patent is subject to a terminal disclaimer.

(21) Appl. No.: 12/727,306

(22) Filed: Mar. 19, 2010

(65) Prior Publication Data

US 2010/0308974 A1    Dec. 9, 2010

Related U.S. Application Data

(63) Continuation-in-part of application No. 12/419,326, filed on Apr. 7, 2009, which is a continuation-in-part of application No. 12/075,858, filed on Mar. 14, 2008.

(60) Provisional application No. 60/918,164, filed on Mar. 15, 2007.

(51) Int. Cl.
*H04Q 5/22* (2006.01)

(52) U.S. Cl.
USPC ...... 340/13.25; 340/10.1; 340/10.3; 340/10.4

(58) Field of Classification Search
USPC ............ 340/10.1, 10.3, 10.4, 13.25; 455/161; 375/373–376
See application file for complete search history.

(56) References Cited

U.S. PATENT DOCUMENTS

| | | | |
|---|---|---|---|
| 3,872,455 A * | 3/1975 | Fuller et al. | 340/870.05 |
| 3,888,708 A | 6/1975 | Wise et al. | |
| 3,943,915 A | 3/1976 | Severson | |
| 4,023,562 A | 5/1977 | Hynecek et al. | |
| 4,026,276 A | 5/1977 | Chubbuck | |
| 4,127,110 A | 11/1978 | Bullara | |
| 4,206,762 A | 6/1980 | Cosman | |

(Continued)

OTHER PUBLICATIONS

The International Bureau of WIPO, International Search Report and Written Opinion of International Searching Authority, Aug. 4, 2008, International Application No. PCT/US08/03475.

(Continued)

*Primary Examiner* — Daniel Wu
*Assistant Examiner* — John Bamert
(74) *Attorney, Agent, or Firm* — McDonald Hopkins LLC

(57) ABSTRACT

A wireless sensor reader is provided to interface with a wireless sensor. The wireless sensor reader transmits a narrowband, fixed frequency excitation pulse to cause the wireless sensor to generate a ring signal. The ring signal corresponds to the value of the physical parameter being sensed. The wireless sensor reader receives and amplifies the ring signal and sends the signal to a phase-locked loop. A voltage-controlled oscillator in the phase-locked loop locks onto the ring signal frequency and generates a count signal at a frequency related to the ring signal frequency. The voltage-controlled oscillator is placed into a hold mode where the control voltage is maintained constant to allow the count signal frequency to be determined. The low power, simple circuitry required to generate the excitation pulse allows the reader to be a small, battery operated unit. Alternative methods of frequency determination are also disclosed.

43 Claims, 17 Drawing Sheets

U.S. PATENT DOCUMENTS

| | | |
|---|---|---|
| 4,385,636 A | 5/1983 | Cosman |
| 4,407,296 A | 10/1983 | Anderson |
| 4,485,813 A | 12/1984 | Anderson et al. |
| 4,511,858 A | 4/1985 | Charavit et al. |
| 4,531,526 A | 7/1985 | Genest |
| 4,644,420 A | 2/1987 | Buchan |
| 4,815,472 A | 3/1989 | Wise et al. |
| 4,881,410 A | 11/1989 | Wise et al. |
| 4,953,387 A | 9/1990 | Johnson et al. |
| 4,966,034 A * | 10/1990 | Bock et al. .................. 73/146.5 |
| 5,005,577 A | 4/1991 | Frenkel |
| 5,006,819 A | 4/1991 | Buchan et al. |
| 5,013,396 A | 5/1991 | Wise et al. |
| 5,046,497 A | 9/1991 | Millar |
| 5,055,838 A | 10/1991 | Wise et al. |
| 5,059,543 A | 10/1991 | Wise et al. |
| 5,108,420 A | 4/1992 | Marks |
| 5,113,868 A | 5/1992 | Wise et al. |
| 5,257,630 A | 11/1993 | Broitman et al. |
| 5,262,127 A | 11/1993 | Wise et al. |
| 5,282,827 A | 2/1994 | Kensey et al. |
| 5,296,255 A | 3/1994 | Gland et al. |
| 5,343,064 A | 8/1994 | Spangler et al. |
| 5,377,524 A | 1/1995 | Wise et al. |
| 5,417,235 A | 5/1995 | Wise et al. |
| 5,564,434 A | 10/1996 | Halperin et al. |
| 5,581,248 A | 12/1996 | Spillman, Jr. et al. |
| 5,690,674 A | 11/1997 | Diaz |
| 5,920,233 A | 7/1999 | Denny |
| 5,992,769 A | 11/1999 | Wise et al. |
| 6,015,386 A | 1/2000 | Kensey et al. |
| 6,025,725 A | 2/2000 | Gershenfeld et al. |
| 6,109,113 A | 8/2000 | Chavan et al. |
| 6,111,520 A | 8/2000 | Allen et al. |
| 6,126,675 A | 10/2000 | Shchervinsky et al. |
| 6,140,144 A | 10/2000 | Najafi et al. |
| 6,174,322 B1 | 1/2001 | Schneidt |
| 6,190,400 B1 | 2/2001 | Van De Moer et al. |
| 6,206,835 B1 | 3/2001 | Spillman, Jr. et al. |
| 6,232,150 B1 | 5/2001 | Lin et al. |
| 6,278,379 B1 | 8/2001 | Allen et al. |
| 6,287,256 B1 | 9/2001 | Park et al. |
| 6,309,350 B1 | 10/2001 | VanTassel et al. |
| 6,331,163 B1 | 12/2001 | Kaplan |
| 6,338,284 B1 | 1/2002 | Najafi et al. |
| 6,447,449 B1 | 9/2002 | Fleischman et al. |
| 6,454,720 B1 | 9/2002 | Clerc et al. |
| 6,471,656 B1 | 10/2002 | Shalman et al. |
| 6,477,901 B1 | 11/2002 | Tadigadapa et al. |
| 6,499,354 B1 | 12/2002 | Najafi et al. |
| 6,570,457 B2 | 5/2003 | Fischer |
| 6,592,608 B2 | 7/2003 | Fisher et al. |
| 6,636,769 B2 | 10/2003 | Govari et al. |
| 6,645,143 B2 | 11/2003 | VanTassel et al. |
| 6,647,778 B2 | 11/2003 | Sparks |
| 6,666,826 B2 | 12/2003 | Salo et al. |
| 6,667,725 B1 | 12/2003 | Simons et al. |
| 6,680,654 B2 | 1/2004 | Fischer et al. |
| 6,682,490 B2 | 1/2004 | Roy et al. |
| 6,713,828 B1 | 3/2004 | Chavan et al. |
| 6,749,622 B2 | 6/2004 | McGuckin, Jr. et al. |
| 6,764,446 B2 | 7/2004 | Wolinsky et al. |
| 6,779,406 B1 | 8/2004 | Kuznia et al. |
| 6,783,499 B2 | 8/2004 | Schwartz |
| 6,824,521 B2 | 11/2004 | Rich et al. |
| 6,838,640 B2 | 1/2005 | Wise et al. |
| 6,844,213 B2 | 1/2005 | Sparks |
| 6,855,115 B2 | 2/2005 | Fonseca et al. |
| 6,890,300 B2 | 5/2005 | Lloyd et al. |
| 6,893,885 B2 | 5/2005 | Lemmerhirt et al. |
| 6,916,310 B2 | 7/2005 | Sommerich |
| 6,923,625 B2 | 8/2005 | Sparks |
| 6,926,670 B2 | 8/2005 | Rich et al. |
| 6,932,114 B2 | 8/2005 | Sparks |
| 6,935,010 B2 | 8/2005 | Tadigadapa et al. |
| 6,939,299 B1 | 9/2005 | Petersen et al. |
| 6,959,608 B2 | 11/2005 | Bly et al. |
| 6,968,743 B2 | 11/2005 | Rich et al. |
| 6,981,958 B1 | 1/2006 | Gharib et al. |
| 7,001,398 B2 | 2/2006 | Carley et al. |
| 7,004,015 B2 | 2/2006 | Chang-Chien et al. |
| 7,013,734 B2 | 3/2006 | Zdeblick et al. |
| 7,028,550 B2 | 4/2006 | Zdeblick et al. |
| 7,048,756 B2 | 5/2006 | Eggers et al. |
| 7,059,176 B2 | 6/2006 | Sparks |
| 7,059,195 B1 | 6/2006 | Liu et al. |
| 7,066,031 B2 | 6/2006 | Zdeblick et al. |
| 7,073,387 B2 | 7/2006 | Zdeblick et al. |
| 7,081,125 B2 | 7/2006 | Edwards et al. |
| 7,137,953 B2 | 11/2006 | Eigler et al. |
| 7,146,861 B1 | 12/2006 | Cook et al. |
| 7,147,604 B1 | 12/2006 | Allen et al. |
| 7,149,587 B2 | 12/2006 | Wardle et al. |
| 7,162,926 B1 | 1/2007 | Guziak et al. |
| 7,192,001 B2 | 3/2007 | Wise et al. |
| 7,198,603 B2 | 4/2007 | Penner et al. |
| 7,211,048 B1 | 5/2007 | Najafi et |
| 7,228,735 B2 | 6/2007 | Sparks et al. |
| 7,245,117 B1 * | 7/2007 | Joy et al. .................. 324/76.53 |
| 7,290,454 B2 | 11/2007 | Liu |
| 7,432,723 B2 | 10/2008 | Ellis et al. |
| 7,466,120 B2 | 12/2008 | Miller et al. |
| 2002/0045921 A1 | 4/2002 | Wolinsky et al. |
| 2002/0072656 A1 | 6/2002 | Vantassel et al. |
| 2002/0115920 A1 | 8/2002 | Rich et al. |
| 2002/0138009 A1 | 9/2002 | Brockway et al. |
| 2002/0151816 A1 | 10/2002 | Rich et al. |
| 2002/0188207 A1 | 12/2002 | Richter |
| 2003/0136417 A1 | 7/2003 | Fonseca et al. |
| 2003/0139677 A1 | 7/2003 | Fonseca et al. |
| 2003/0139771 A1 | 7/2003 | Fisher et al. |
| 2003/0158584 A1 | 8/2003 | Cates et al. |
| 2003/0191496 A1 | 10/2003 | Edwards et al. |
| 2004/0102806 A1 | 5/2004 | Broome et al. |
| 2004/0158138 A1 | 8/2004 | Kilcoyne et al. |
| 2004/0220637 A1 | 11/2004 | Zdeblick et al. |
| 2004/0255643 A1 | 12/2004 | Wise et al. |
| 2004/0260164 A1 | 12/2004 | Kilcoyne et al. |
| 2005/0013685 A1 | 1/2005 | Ricketts et al. |
| 2005/0015014 A1 | 1/2005 | Fonseca et al. |
| 2005/0043601 A1 | 2/2005 | Kilcoyne et al. |
| 2005/0049634 A1 | 3/2005 | Chopra |
| 2005/0080346 A1 | 4/2005 | Gianchandani et al. |
| 2005/0090719 A1 | 4/2005 | Scheiner et al. |
| 2005/0103114 A1 | 5/2005 | Bly et al. |
| 2005/0154321 A1 | 7/2005 | Wolinsky et al. |
| 2005/0160825 A1 | 7/2005 | Zdeblick et al. |
| 2005/0160827 A1 | 7/2005 | Zdeblick et al. |
| 2005/0187482 A1 | 8/2005 | O'Brien et al. |
| 2005/0228308 A1 | 10/2005 | Iddan et al. |
| 2005/0288596 A1 | 12/2005 | Eigler et al. |
| 2005/0288604 A1 | 12/2005 | Eigler et al. |
| 2005/0288722 A1 | 12/2005 | Eigler et al. |
| 2006/0047205 A1 | 3/2006 | Ludomirsky et al. |
| 2006/0052821 A1 | 3/2006 | Abbot et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0116590 A1 | 6/2006 | Fayram et al. |
| 2006/0122522 A1 | 6/2006 | Chavan et al. |
| 2006/0129050 A1 | 6/2006 | Martinson et al. |
| 2006/0161171 A1 | 7/2006 | Schwartz |
| 2006/0177956 A1 | 8/2006 | O'Brien et al. |
| 2006/0178583 A1 | 8/2006 | Montegrande et al. |
| 2006/0178695 A1 | 8/2006 | Decant, Jr. et al. |
| 2006/0206146 A1 | 9/2006 | Tenerz |
| 2006/0212047 A1 | 9/2006 | Abbot et al. |
| 2006/0217762 A1 | 9/2006 | Meahs et al. |
| 2006/0217763 A1 | 9/2006 | Abbott et al. |
| 2006/0217764 A1 | 9/2006 | Abbott et al. |
| 2006/0229488 A1 | 10/2006 | Ayre et al. |
| 2006/0241354 A1 | 10/2006 | Allen |

| | | |
|---|---|---|
| 2006/0271078 A1 | 11/2006 | Modesitt |
| 2006/0287602 A1 | 12/2006 | O'Brien et al. |
| 2007/0007240 A1 | 1/2007 | Wise et al. |
| 2007/0028698 A1 | 2/2007 | Guziak et al. |
| 2007/0032734 A1 | 2/2007 | Najafi et al. |
| 2007/0049980 A1 | 3/2007 | Zielinski et al. |
| 2007/0049984 A1 | 3/2007 | Osypka |
| 2007/0060959 A1 | 3/2007 | Salo et al. |
| 2007/0073351 A1 | 3/2007 | Zielinski et al. |
| 2007/0088388 A1 | 4/2007 | Opolski et al. |
| 2007/0100215 A1 | 5/2007 | Powers et al. |
| 2007/0106246 A1 | 5/2007 | Modesitt |
| 2007/0106328 A1 | 5/2007 | Wardle et al. |
| 2007/0106333 A1 | 5/2007 | Fernandez |
| 2007/0112358 A1 | 5/2007 | Abbott et al. |
| 2007/0118039 A1 | 5/2007 | Bodecker et al. |
| 2007/0149880 A1 | 6/2007 | Willis |
| 2007/0160748 A1 | 7/2007 | Schugt et al. |

OTHER PUBLICATIONS

The International Bureau of WIPO, International Search Report and Written Opinion of International Searching Authority, Aug. 25, 2010, International Application No. PCT/US10/27951.

Haynes, H.E. & Witchey, A.L., Medical Electronics: The Pill That "Talks", DEP, pp. 52-54, Camden, N.J.

Collins, Carter, Miniature Passive Pressure Transensor for Implanting in the Eye, Transactions on Bio-Medical Engineering, vol. BME-14, No. 2, pp. 74-83, Apr. 1967.

Nagumo, J., Uchiyama, A., Kimoto, S., Watanuki, T., Hori, M., Suma, K., Ouchi, A., Kumano, M., and Watanabe, H., Echo Capsule for Medical Use (A Batteryless Endoradiosonde), IRE Transaction on Bio-Medical Electronics, pp. 195-199, 1962.

Haynes, H.E. & Witchey, A.L., Medical Electronics; The Pill That "Talks" DEP, 1960, pp. 52-54, Cambden, NJ.

\* cited by examiner

US 8,493,187 B2

WIRELESS SENSOR READER

RELATED APPLICATIONS

This non-provisional application is a continuation-in-part of U.S. patent application Ser. No. 12/419,326 filed on Apr. 7, 2009 which is a continuation-in-part of U.S. patent application Ser. No. 12/075,858 filed on Mar. 14, 2008, which claims priority to U.S. Provisional Application No. 60/918,164 filed on Mar. 15, 2007, each of which is hereby incorporated by reference.

TECHNICAL FIELD

This invention relates generally to reading passive wireless sensors, and more particularly to a reader circuitry and a method for exciting and sensing data from passive wireless sensors.

BACKGROUND

Passive wireless sensor systems that employ resonant circuit technology are known. These systems utilize a passive wireless sensor in remote communication with excitation and reader circuitry. Often the wireless sensor is implanted at a specific location, such as within the human body, to detect and report a sensed parameter. The sensed parameter varies the resonant circuit frequency of the wireless sensor. The reader device samples the resonant frequency of the wireless sensor to determine the sensed parameter.

Early researcher Haynes (H. E. Haynes and A. L. Witchey, "Medical electronics, the pill that 'talks'", *RCA Engineer*, vol 5, pp. 52-54. 1960) discloses an ingestible pill incorporating a wireless pressure sensor, with a large reader device surrounding the subject's body and measuring frequency by means of a discriminator circuit. Nagumo (J. Nagumo, A. Uchiyama, S. Kimoto, T. Watanuki, M. Hori, K. Suma, A. Ouchi, M. Kumano, and H. Watanabe, "Echo capsule for medical use (a batteryless radioendosonde)", *IRE Transactions on Bio-Medical Electronics*. vol. BME-9, pp. 195-199, 1962) discloses a similar system, in which the sensor includes an energy storing capacitor to power the sensor during resonance.

U.S. Pat. No. 4,127,110 by Bullara discloses a sensor for measuring brain fluid pressure. U.S. Pat. No. 4,206,762 by Cosman discloses a similar sensor for measuring intra-cranial pressure. Specifically, the Cosman patent describes the use of a grid dip system for wirelessly measuring the resonant frequency of the sensor.

Several methods of reading passive wireless sensors have also been described in prior patents. For example, the Cosman patent discloses an external oscillator circuit that uses the implanted sensor for tuning, and a grid dip measurement system for measurement of sensor resonant frequency. U.S. Pat. No. 6,015,386 by Kensey, et al., discloses a reader that excites the passive sensor by transmitting frequency sweeps and uses a phase detector on the transmit signal to identify the point during the sweep at which the transmitted frequency matches the resonant frequency of the sensor. U.S. Pat. No. 6,206,835 by Spillman, et al., discloses a medical implant application for reader technology disclosed in U.S. Pat. No. 5,581,248 by Spillman, et al. This reader technology detects a frequency dependent variable impedance loading effect on the reader by the sensor's detected parameter. U.S. Pat. No. 7,432,723 by Ellis, et al., discloses a reader with energizing loops each tuned to and transmitting different frequencies spaced to ensure that the bandwidth of the sensor allows resonant excitation of the sensor. Ellis uses a ring-down response from the appropriate energizing loop to determine the sensor resonant frequency. U.S. Pat. No. 6,111,520 by Allen, et. al., discloses a method of transmitting a "chirp" of white noise to the sensor and detecting the ring-down response.

Some readers utilize phased-locked-loop ("PLL") circuitry to lock onto the sensor's resonant frequency. U.S. Pat. No. 7,245,117 by Joy, et al. discloses an active PLL circuit and signal processing circuit that adjusts a transmitting PLL frequency until the received signal phase and the transmitting PLL signal phase match. When this match occurs, the transmitting PLL frequency is equal to the sensor resonant frequency.

PLL circuits may incorporate sample and hold (S/H) functions to sample the input frequency and hold the PLL at a given frequency. PLLs with S/H may be used in a variety of applications. For example, U.S. Pat. No. 4,531,526 by Genest discloses a reader that uses a PLL circuit with a S/H circuit to adjust the transmitted frequency of the reader to match the resonant frequency received from the sensor. This is done to maximize sensor response to the next transmission and measures the decay rate of the sensor resonance amplitude to extract the sensed parameter value. U.S. Pat. No. 4,644,420 by Buchan describes a PLL with a S/H used to sample a tape data stream and maintain an appropriate sampling frequency for evaluation of digital data pulses on the tape. U.S. Pat. No. 5,006,819 by Buchan, et al., provides additional enhancements to this concept. U.S. Pat. No. 5,920,233 by Denny describes a high-speed sampling technique using a S/H circuit with a PLL to reduce the charge pump noise from the phase-frequency detector to enhance the low-jitter performance of a frequency synthesizing circuit. U.S. Pat. No. 4,511,858 by Charavit, et al., discloses a PLL with a S/H circuit to pre-position the control voltage of a voltage controlled oscillator when the PLL lock frequency is being changed. This is done to enhance the response speed of the PLL when changing the desired synthesized frequency. U.S. Pat. No. 6,570,457 by Fischer and U.S. Pat. No. 6,680,654 by Fischer, et al., disclose a PLL with S/H circuitry to enhance PLL frequency stepping, as well as an offset correction feature. U.S. Pat. No. 3,872,455 by Fuller, et al. discloses a PLL having a digital S/H to freeze the frequency display and preload the frequency counter when a PLL phase lock is detected.

Readers have also been found that implement direct signal sampling and frequency analysis techniques. One example is U.S. Pat. No. 7,048,756 by Eggers, et al., which measures internal body temperature using a resonant sensor with a curie temperature to show response change at a temperature threshold.

Further, readers using digital signal analysis to improve performance and response are known. U.S. Pat. No. 7,466,120 by Miller, et al., describes using a digital signal processor (DSP) to evaluate the response of a passive blood pressure sensor that has been excited by a frequency pulse then evaluating response signals from a triple-frequency excitation for relative phase delays.

Current designs for passive sensor readers, such as those disclosed above, suffer from a number of deficiencies. The early "pulsed echo ringing systems" of Haynes and Nagumo required large, high-powered reader devices. Additionally, Collins (C. Collins, "Miniature Passive Pressure Transensor for Implanting in the Eye", *IEEE Transactions on Bio-Medical Engineering*, vol BME-14, no. 2, April 1967) discloses that these systems suffered from inaccuracy and poor resolution due to difficulties in measuring the short-lived ring signal frequency, leading to their abandonment in favor of various swept-frequency methods.

Swept frequency sensor readers similar to those described in the Cosman, Kensey, Ellis and Spillman patents, as well as the pulse method described by Allen, require relatively wide bandwidth allowance by the government body regulating radio transmissions. This limits other uses of the spectrum and makes interference a potential issue. Readers that track the resonant frequency of a passive resonant sensor with a variable frequency transmitter, such as Genest, Ellis, and Joy also suffer from similar problems. The additional circuitry required by swept-frequency and/or digital tracking approaches is significant, adding to reader size, cost, and failure rate. Moreover, the amount of electrical power needed for transmissions, signal processing, sampling, and tracking the resonant frequency of a sensor using digitally controlled frequency tracking or swept frequency systems is significant and limits the ability to use battery power in a reader, as well as limiting the longevity of batteries in a battery powered reader. Accordingly, an improved passive sensor and reader system is needed in the art.

BRIEF DESCRIPTION OF THE DRAWINGS

Reference to the detailed description is taken in connection with the following illustrations.

SUMMARY

Figure 1:
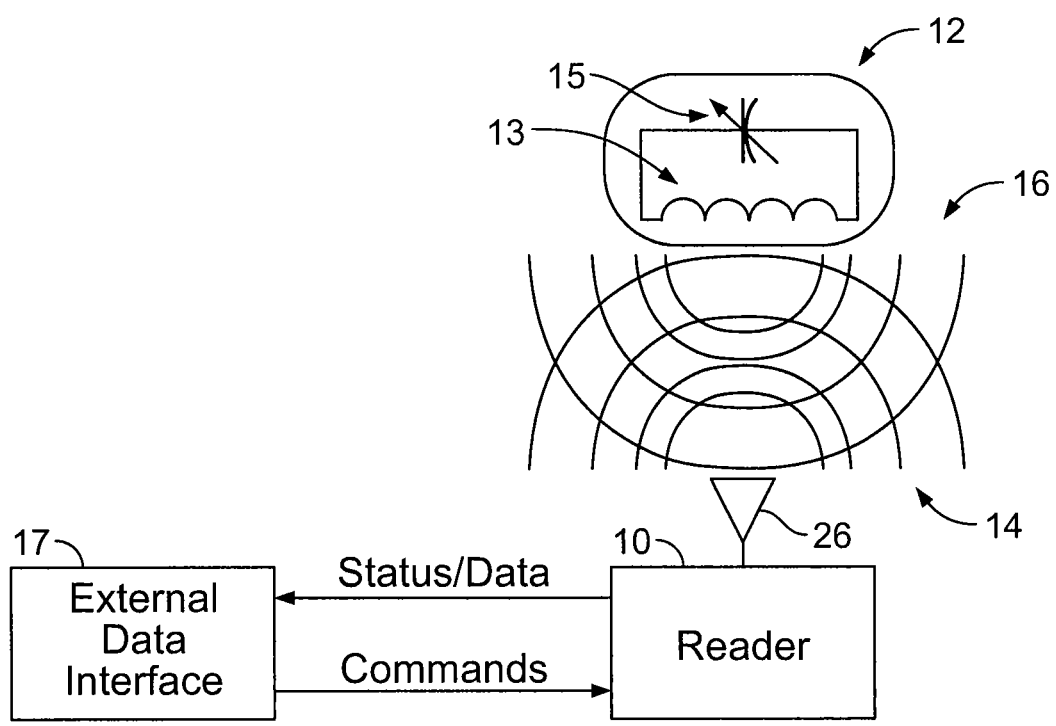
FIG. 1 is a block diagram of a passive wireless sensor system.

A reader device is provided to interface with a wireless sensor, whose resonant frequency varies proportionately with the sensed parameter. The reader transmits a short pulse of energy at a fixed frequency to cause the wireless sensor to ring at or near its resonant frequency immediately after the transmission ends. The reader receives and amplifies the sensor ring signal, and measures its frequency. In one embodiment, the reader carries out this measurement by sending the signal to a phase-locked loop ("PLL") that locks to the sensor ring frequency. Once the PLL has locked to the ring frequency, the PLL's voltage controlled oscillator ("VCO") is placed in a hold mode to maintain the VCO frequency at the locked frequency. The VCO frequency is counted to determine the sensor resonant frequency. Alternately, the VCO control voltage itself is sampled and is used to determine sensor resonant frequency based on a known correlation. When VCO control voltage is sampled, the VCO frequency may not need to be locked if the voltage sampling is sufficiently fast. Further frequency determination methods and systems involving digital spectrum analysis are also disclosed.

DETAILED DESCRIPTION

A passive wireless sensor system including a reader 10 in remote communication with a sensor 12 is provided. The reader 10 is capable of exciting the sensor 12 by transmitting a signal, such as a radio frequency ("RF") pulse, at or near the resonant frequency of the sensor 12. (See FIG. 1.) The sensor 12 may emit a ring signal for a short period of time in response to the excitation pulse from the reader 10.

The sensor 12 may be a passive device, containing no power source of its own, and capable of emitting a ring signal 16 in response to an excitation signal 14 at or near the resonant frequency of the sensor 12. The sensor 12 may be configured to sense a specific parameter. For example, the sensor 12 may include a fixed inductor 13 and a capacitor 15 that varies based on the sensed parameter. The varying capacitance or inductance alters the resonant frequency of the sensor 12. It should be appreciated, however, that the sensor 12 may be any wireless sensor known in the art capable of remote communication with the reader 10. Further, while the sensor 12 is described as an RF resonant sensor, it will be appreciated that the sensor 12 may be an acoustically resonant sensor, optically resonant sensor, or other similar sensor known in the art. The reader 10 may employ corresponding signals to activate the sensor 12. Further, the sensor 12 may be an active sensor or a passive sensor.

In an embodiment, sensor 12 comprises at least one inductive element 13 and one capacitive element 15. To vary sensor 12's resonant frequency in proportion to the sensed parameter, either inductive element 13, or capacitive element 15, or both, may be configured to change inductance or capacitance proportionately with the sensed parameter. In an example embodiment shown in FIG. 1, capacitive element 15 is variable and inductive element 13 is fixed. Typical examples of such components are sensors which change their capacitance in response to changes in pressure. Such capacitive pressure sensors are well known in the art.

In one embodiment, the at least one inductive element 13 in sensor 12 also functions as an antenna for sensor 12, coupling energy to and from another antenna 26 located on the reader 10.

The reader 10 may excite the sensor 12 by transmitting an excitation pulse 14 in the vicinity of the sensor 12. For example, the reader may emit a RF excitation pulse 14 at or near the resonant frequency of the sensor 12. The sensor 12 may emit a ring signal 16 in response to the excitation pulse 14. The reader 10 may determine the frequency of the ring signal 16 in order to determine the sensed parameter value.

Figure 2:
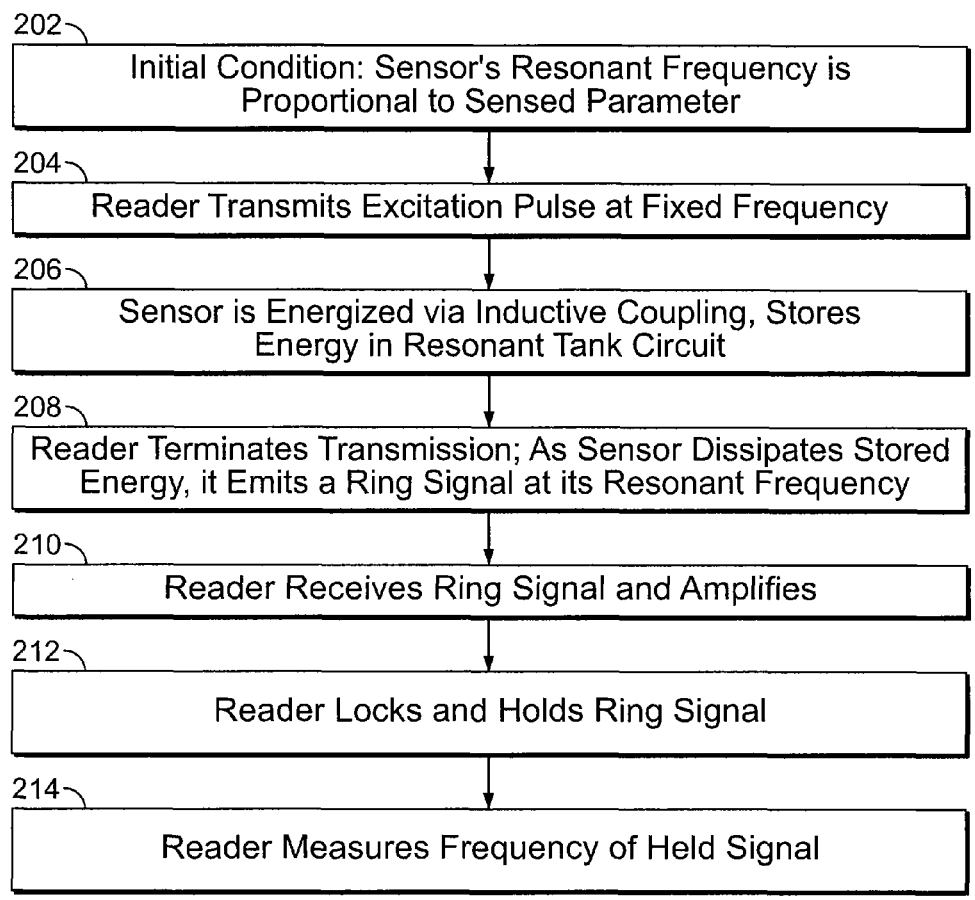
FIG. 2 is a flow diagram illustrating the process of acquiring a reading from the sensor.

FIG. 2 is a flow diagram illustrating an example of the steps that may be involved in the process of the reader 10 acquiring a reading from the sensor 12. Each step may consist of multiple indented steps and such steps may be indented several levels. However, only basic, top-level steps are shown to clarify the sequence of operation of the reader during reading acquisition. In the initial condition 202, the sensor 12 is already configured such that its resonant frequency is proportional to the sensed parameter. Some examples of sensed parameters that can be measured with capacitive or inductive sensors are pressure, temperature, acceleration, angular rate, PH level, glucose level, salinity, viscosity, dielectric constant, humidity, proximity, electrolyte level, and oxygen level. Additionally, other known parameters may also be sensed.

The sensor 12 is located remotely from the reader 10. In one embodiment, the sensor 12 is implanted inside a living human or animal body to take physiological measurements. Possible locations of interest include, but are not limited to: blood vessels, cranium, eyes, bladder, stomach, lungs, heart, muscle surface, bone surface, or any bodily cavity. The sensor 12 may be implanted for short-term acute, or long-term chronic time periods. The sensor 12 may be standalone, or may be incorporated with another device such as a catheter, stent, shunt, filter, pacemaker, pacemaker wire, vascular closure device, and the like.

The sensor 12 is designed to have an operating frequency range 220 (not shown in FIG. 2) that maps to a range of values of the sensed parameter. When it is desired to acquire a reading, the reader 10 may transmit an excitation pulse 14 in the vicinity of the sensor 12 as in block 204 of FIG. 2. The pulse 14 may be a brief burst of energy at a predetermined fixed frequency. The pulse 14 frequency may be selected to be at or near the middle of the sensor 12 operating frequency range 220, and the bandwidth of the pulse 14 may be narrow. An advantage of a narrow bandwidth pulse is that it is less likely to interfere electromagnetically with other devices around it. A further advantage of a narrow bandwidth pulse is that it allows the system to comply more readily with government or industry regulations regarding electromagnetic spectrum allocation, by enabling system designers to select a pulse frequency within a tight band specified by such regulations. In one embodiment, the pulse 14 is narrow and centered at 13.56 MHz, which is one of the so-called Industrial, Scientific, and Medical (ISM) bands allocated for use in commercial RF devices by the International Telecommunications Union (ITU). Yet another advantage of a narrow bandwidth pulse is that it may require less power than an equivalent continuous-transmit solution, thus making reader 10 more amenable to battery operation, and allowing the use of smaller components which generally require less heatsinking than their higher powered counterparts. Finally, an advantage of transmitting a fixed frequency pulse 14 in step 204 of FIG. 2 is that the transmit circuitry of reader 10 is simple compared to swept-frequency or continuous-transmit solutions.

Because sensor 12 is in close proximity to reader 10, step 206 of FIG. 2 now takes place. Sensor 12 is energized by pulse 14 via inductive coupling between its antenna and that of reader 10. Pulse 14 causes current to flow in the antenna of sensor 12, energizing the 'LC Tank' circuit formed by capacitor 15 and inductor 13. Pulse 14 is generally of short duration, and in step 208, reader 10 abruptly terminates pulse 14. Immediately the energy stored in the LC tank circuit of sensor 12 begins to dissipate, oscillating at sensor 12 resonant frequency as it does so. The sensor 12 antenna thus emits a ring signal 16 at this frequency. After terminating transmission, the reader 10 must immediately go into a receiving mode, as in step 210, in order to detect ring signal 16 and amplify it.

Depending on measurement conditions, the ring signal may be weak, noisy, or of short duration, leading to accuracy and resolution penalties during frequency measurement. For this reason, the reader 10 may lock and hold the sampled ring signal at constant frequency and strong amplitude in step 212, for a sufficient time to acquire a high accuracy frequency measurement in step 214.

Figure 3:
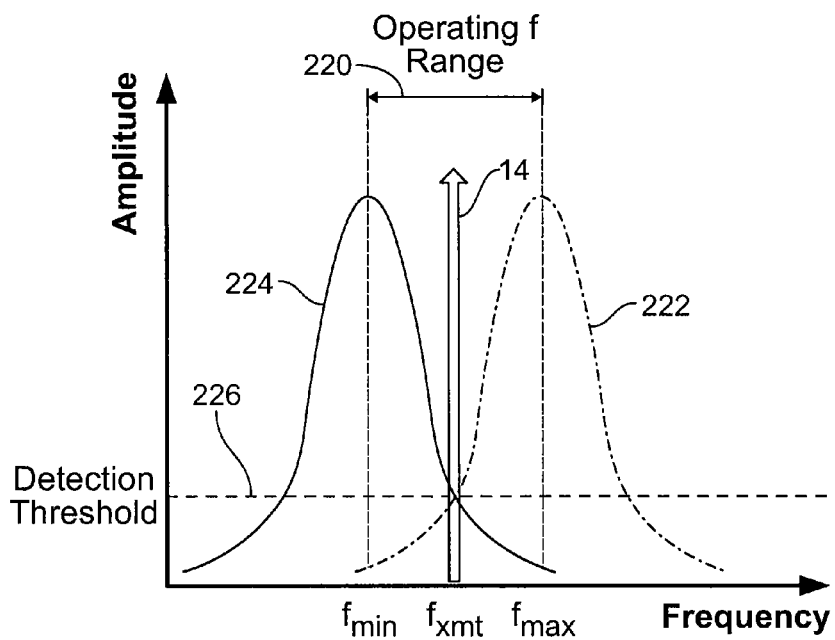
FIG. 3 is a plot qualitatively illustrating the frequency characteristics of the signal exchange between the sensor and the reader.

FIG. 3 illustrates qualitatively the idealized characteristics of the reader 10 and sensor 12 in the frequency domain, in an embodiment. Sensor 12 senses its physical parameter of interest across a predetermined operational range of values. It maps this physical parameter range onto a corresponding operating frequency range 220. Curve 224 is the transfer function of the sensor 12, when the resonant frequency of sensor 12 is at the minimum of its operating frequency range 220. Sensor transfer function 224 has its peak at the resonant frequency of sensor 12. As the sensed parameter varies within the operational range of values, the sensor transfer function moves correspondingly within operating frequency range 220. Thus, depending on the value of the sensed physical parameter, the sensor transfer function can be centered anywhere within operating frequency range 220. Its resonant frequency (peak of the transfer function curve) will correspond to the value of the sensed parameter. When the sensed parameter is at the other extreme of its operational range, the sensor transfer function becomes the maximum frequency sensor transfer function 222.

Narrowband function 14 in FIG. 3 represents the excitation pulse 14 shown in FIG. 1. Its frequency, designated $f_{xmt}$, is generally fixed to be at or near the center of operating frequency range 220. Pulse 14 is generally of narrow bandwidth, short time duration, and is fixed at a predetermined frequency $f_{xmt}$. These pulse characteristics endow reader 10 with several advantages over readers which must sweep or vary their transmitted frequencies: simpler circuitry, simpler control software/firmware, lower overall power consumption (enabling battery operation), lower power (thus smaller) components, less internal heat dissipation, reduced susceptibility to electromagnetic interference from an outside source, reduced likelihood of interfering electromagnetically with an outside device, and increased ease of compliance with government frequency allocation regulations.

Another important feature shown in FIG. 3 is the horizontal line representing the minimum signal detection threshold 226 of the reader 10. After excitation pulse 14 is switched off, sensor 12 will dissipate the energy it received from excitation pulse 14. In the absence of the forced excitation pulse 14, this energy causes oscillation at the sensor 12 resonant frequency, emitting a ring signal 16 (not shown in FIG. 3). The signal strength (amplitude) of ring signal 16 is determined by the intersection of the excitation pulse 14 and the sensor transfer function: the ring signal's amplitude will be limited by the product of the two functions at that point. The amplitude of this product, at the point of intersection, must be greater than or equal to the signal detection threshold 226 of reader 10 in order for the ring signal 16 to be detected and measured by the reader 10.

Figure 4A:
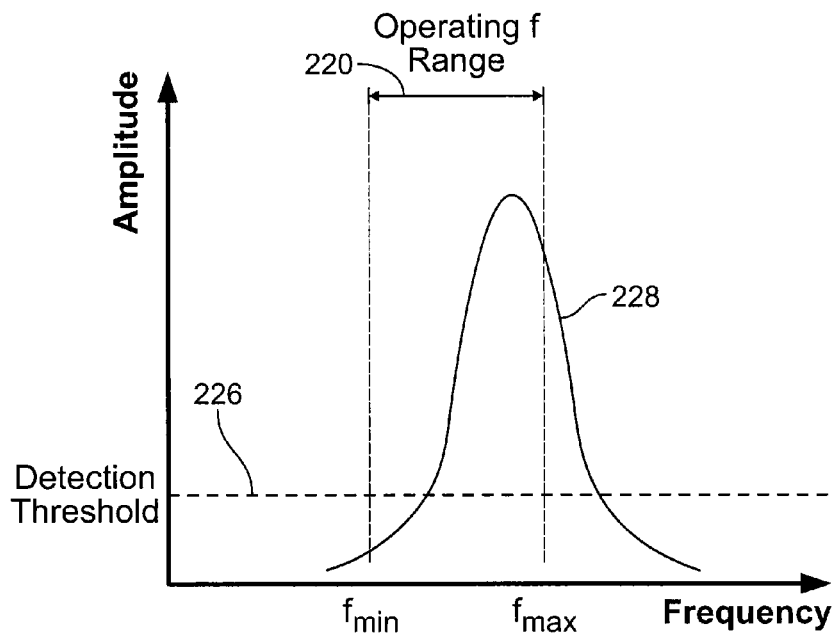
FIG. 4 comprises three sequential plots qualitatively illustrating the frequency characteristics of the signal exchange between sensor and reader during a reading acquisition.

FIG. 4 provides an illustrative example, in the frequency domain, of a typical signal exchange between reader 10 and sensor 12. The process shown in this figure is the same as that shown in flowchart form in FIG. 2. In the initial condition shown in FIG. 4a, the sensed parameter value is such that sensor 12 transfer function 228 is centered at a frequency within the operating frequency range 220. Note that the sensed parameter (and hence transfer function 228) changes on a much slower timescale than the electronic signals going between sensor 12 and reader 10, and hence transfer function 228 is quasistatic relative to those signals. Because the sensed parameter is quasistatic related to the electronic signals, the reader 10 is able to take multiple samples over a short time interval and average those samples to obtain a more accurate measurement.

Figure 4B:
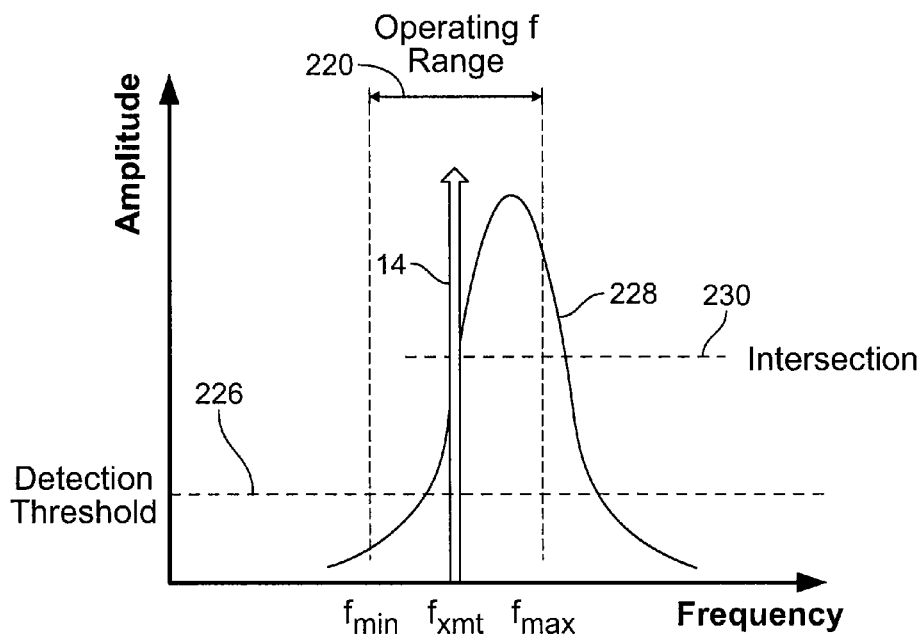

In FIG. 4b, excitation pulse 14 is generated by reader 10. Pulse 14 is a narrow bandwidth signal, centered at frequency $f_{xmt}$, which is at or near the center of operating frequency range 220. When reader 10 generates excitation pulse 14 in the physical vicinity of sensor 12, energy is transferred from reader 10 to sensor 12. In one embodiment, this energy transfer occurs by inductive coupling, with $f_{xmt}$ in the RF frequency band. Note the point of intersection 230 between reader excitation pulse 14 and sensor transfer function 228. The product of the two amplitudes at this point will determine the amplitude of the ring signal 16.

Figure 4C:
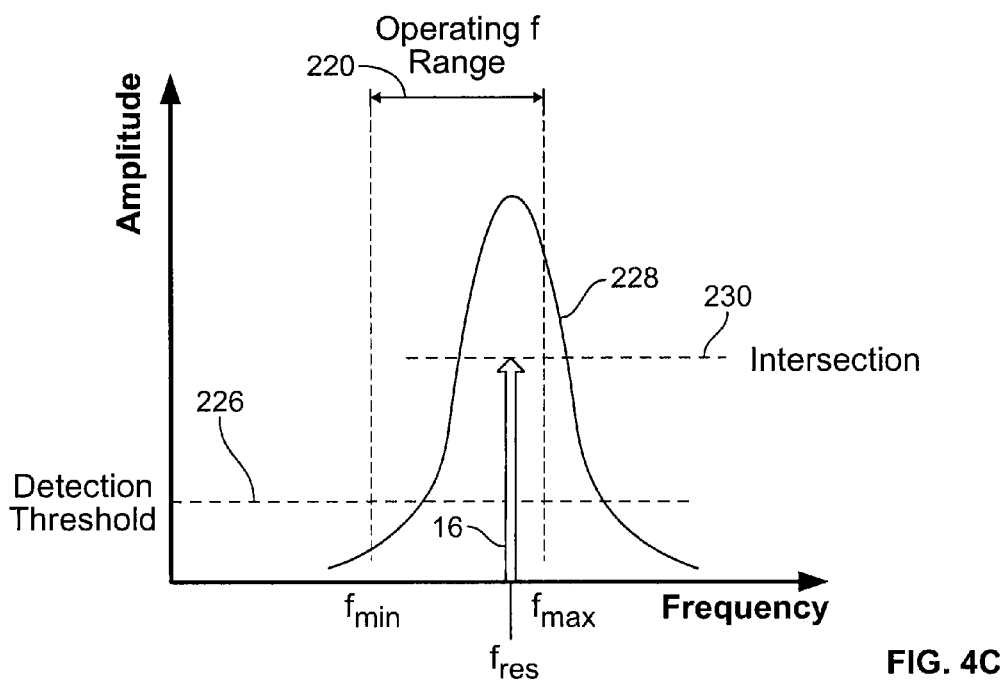

Next, in FIG. 4c, reader 10 stops transmitting excitation pulse 14. When excitation energy ceases, the sensor 12 shifts from a forced drive characteristic at the transmit frequency with phase error due to off-transmit-frequency resonance, to a passive resonant characteristic at a frequency dependent on the resonant frequency of the sensor and its surroundings, approximately at the peak of curve 228. Due to resonant energy within the inductor of the sensor 12, a time-varying magnetic field is generated around the sensor 12 at this resonant frequency, which can be detected at the reader 10 as an emitted signal at this resonant frequency.

Note that if sensor 12 is exposed to a sensed parameter that moves transfer function 228 still further to the right in FIG. 4b (in the direction of increasing $f_{res}$) then the amplitude of the curve 228 at the point of $f_{xmt}$ decreases, causing intersection level 230 to decrease as well. As $f_{res}$ increases further and reaches $f_{max}$, intersection amplitude 230 equals reader 10's minimum detection threshold 226. If transfer function 228 moves still further to the right, $f_{res}$ exceeds $f_{max}$, and the intersection amplitude 230 falls below the detection threshold 226 of reader 10. Now reader 10 can no longer detect the ring signal 16, i.e. $f_{res}$ is outside the operating frequency range 220 of the system. Note that sensor 12 must be designed such that its transfer function 228 has wide enough bandwidth to maintain an intersection amplitude 230 above the detection threshold 226 of reader 10 across the entire operating frequency range 220. However, designing sensor 12 with a wide transfer function 228 generally lowers the peak amplitude of transfer function 228, so a balance must be found between amplitude and bandwidth. In general, it is clear from FIG. 4 that the reader 10's ability to detect and measure ring signal 16 will also depend on the power level of the ring signal after cessation of excitation pulse 14, on the system Q, and the time duration of ring signal 16.

The shapes of transfer function 228, signals 14 and 16, and the operating range 220 shown in FIG. 4 are illustrated as examples. In some embodiments, transfer function 228 may have different characteristics, and may not be symmetrical about $f_{res}$, which is at its peak. Additionally, operating range 220 may not be symmetrical about $f_{xmt}$, the frequency of excitation pulse 16. Operating range 220 asymmetry may occur as a result of the sensor 12 characteristics, or may be purposely designed in, in order to offset asymmetries in transfer function 228, excitation signal 16, or ring signal 14.

In an alternate embodiment, reader 10 may transmit a pulse which is not near the center of the sensor 12 operating range 220. In this case reader 10 transmits a pulse at a frequency that is harmonically related to a frequency inside operating range 220 of sensor 12. That is, a higher or lower harmonic resulting from the transmitted pulse or pulses is used as the excitation pulse 16 shown in FIG. 4.

In yet another embodiment, reader 10 may transmit two or more excitation pulses at different frequencies, either simultaneously or at different times. These multiple excitation pulses may excite different parts of the operating frequency range 220. Alternatively, frequencies created by adding or subtracting combinations of these multiple pulses, or their harmonics, may serve as the excitation frequency 16 in FIG. 4. Excitation pulses may also assume a Gaussian, or other non-sinusoidal shape.

Referring again to FIG. 1, reader 10 may also incorporate circuitry for converting the ring frequency readings from sensor 12 to digital form, and storing these in an on-board memory. Besides measurements from sensor 12, reader 10's memory may also store other relevant data. Examples include timestamp data, calibration coefficients, firmware required to accomplish system functions, firmware upgrades, part numbers, serial numbers, usage logs, historical data, configuration data, diagnostic data, information about the host location and application of the sensor, and user-defined data.

Reader 10 may also incorporate human interfaces such as a display screen, LEDs, or an audible indication, corresponding to some aspect of the frequency data. Further, reader 10 may process the frequency data it receives, performing such functions as averaging, filtering, curve-fitting, threshold monitoring, timestamping, trend analysis, comparison with other data, and the like.

Figure 5:
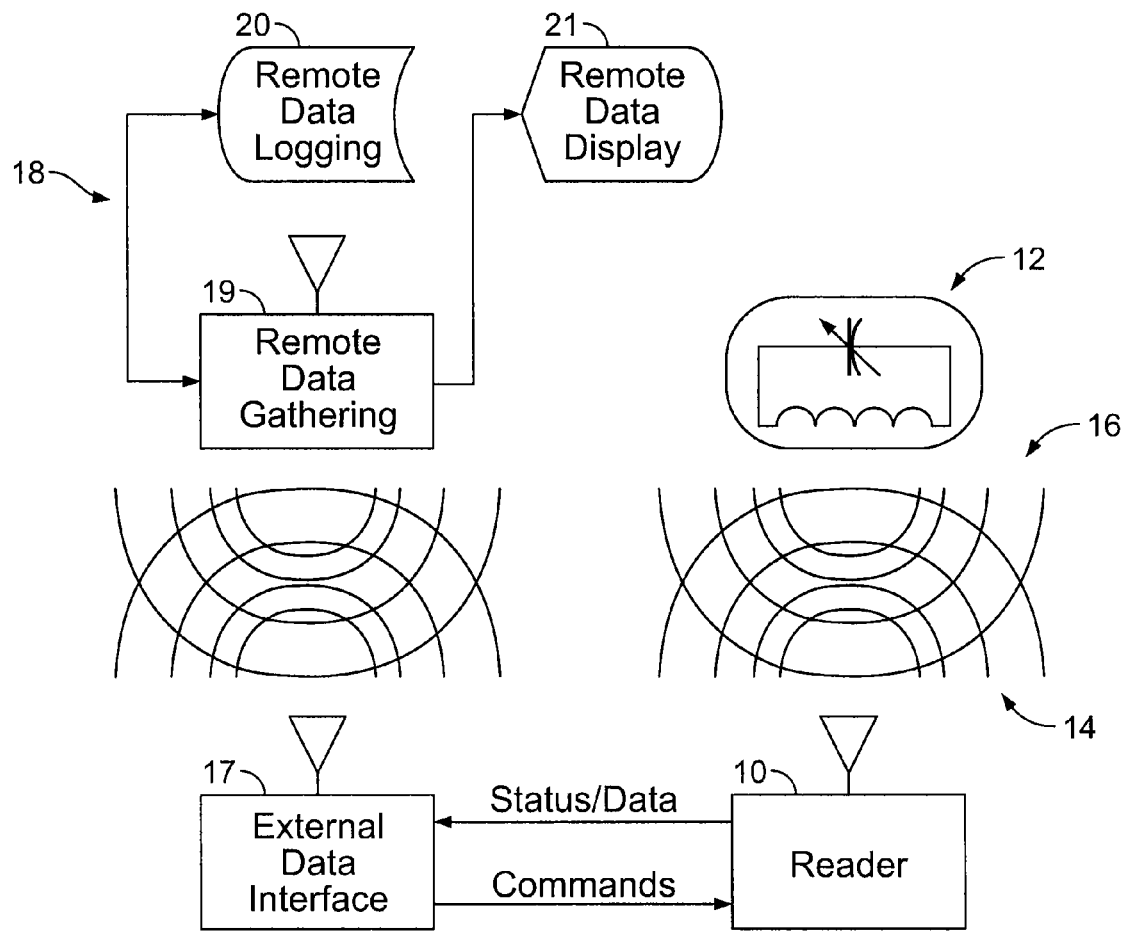
FIG. 5 is a block diagram of the passive wireless sensor system of FIG. 1, expanded to include an external data interface and remote data handling functions.

Reader 10 may also communicate with a data interface 17, as shown in FIG. 5. Data interface 17 is external to reader 10, and is configured to receive electronic signals from reader 10, and transmit signals to reader 10. Additionally, data interface 17 may provide power to reader 10, for example charging a battery located in reader 10. Examples of data interface 17 include a host computer, a docking station, a telephone network, a cell phone network, a GPS network, an optical network, a Bluetooth network, a storage area network, an internet website, a remote database, a data input device, an audible sound, and a display screen.

The reader 10 and data interface 17 may be connected directly to one another or indirectly through an intermediate device, or may communicate via a remote connection. They may reside in the same housing. The reader 10 and data interface 17 may be connected via a cable or by a wireless link. The reader 10 may send information to the data interface 17. Examples include data related to the sensor 12, measurements taken from sensor 12, timestamp data, part number, serial number, firmware revision information, usage logs, diagnostic data, historical data, status data, configuration data, information about the host location and application of the sensor, and user-defined data. The data interface 17 may provide data and commands to the reader 10. For example, the data interface 17 may provide reader 10 with information regarding schedules and intervals for sampling the sensor 12, calibration coefficients or lookup tables, firmware required to accomplish system functions, firmware upgrades, configuration settings, diagnostic commands, resets, restarts, user-defined data, and user-issued commands.

The data interface 17 may further communicate with a remote data system 18 to exchange status and control signals, as well as provide sensor data. The remote data system 18 may include a data gathering module 19 to receive data from the data interface 17, a data logging module 20 to store the received data, and a data display 21 to display the sensor data. Like the data interface 17, the remote data system 18 may store and process the data, issue commands, and distribute these data and commands, allowing communication with multiple users over a data network. Like the connection between reader 10 and data interface 17, the connection between data interface 17 and remote data system 18 may be through a cable or may be wireless. The configuration shown in FIG. 5, where the reader 10 connects to data interface 17 through a cable, and data interface 17 connects to remote data system 18 wirelessly, is one example embodiment. Although the example in FIG. 5 associates the functions of data logging and display with remote data system 18, it will be obvious to those of normal skill in the art that these functions may also be carried out by external data interface 17 or reader 10.

The system of reader 10, sensor 12, and data interface 17 described above is particularly advantageous in one embodiment in the field of biomedical telemetry. In this embodiment sensor 12 is implanted into a living human being, to sense a physiological parameter, for example blood pressure sensed from within an artery. Sensor 12 is well-suited for this application as it can be made very small by conventional techniques, and as it is a passive sensor it requires no on-board power source that will eventually be exhausted. Reader 10, for its part, can be physically small enough to be handheld, battery-powered, thermally cool, and electromagnetically compatible with other electronics in its vicinity. These attributes stem from the simple, low-power circuits that generate the narrowband, fixed frequency excitation pulse 14 as described above. Thus reader 10 may be worn comfortably on a person's clothing in the vicinity of the implanted sensor 12, taking frequent readings and processing/storing them. Periodically, for example daily, the user may place reader 12 on data interface 17 in the form of a docking station. Data interface 17 may contain circuitry to charge the reader 12 battery, update reader 12 settings and software, and download its data. Data interface 17 may also communicate this data to the user, and other interested persons such as the user's physician, via an internet or telephone link. Because of the low-power excitation scheme used by reader 12, such a system can take frequent, accurate blood pressure readings with a minimum of inconvenience to a patient, and communicate these to caregivers efficiently. Clearly, this embodiment is also applicable to sensing any other internal physiological parameter which can effect a change in resonant frequency on a passive LC sensor.

In a variation of this embodiment, sensor 12 is incorporated with another implantable medical device that performs a different function. For example, sensor 12 may be a blood pressure sensor incorporated with a vascular closure device, such as the Angio Seal product from St. Jude Medical, Inc, of St. Paul, Minn. In yet another variation of this embodiment, reader 10 may be incorporated with another device. For example, reader 10 may be attached to a cell phone, a pair of glasses, a handheld music player, a video game, an article of clothing, or a wristwatch.

Sensor 12, comprising capacitor 15 and inductor 13, may be such that these circuit elements are assembled in a single package. Alternatively, some applications may make it advantageous to locate capacitor 15 away from inductor 13, with the two elements connected by conductive leads. As an example, in the embodiment where sensor 12 is implanted in a human body, the pressure-sensitive capacitor 15 might be located at the site where the pressure of interest is found, and the inductor 13, which acts as an antenna, might be located closer to the skin surface, minimizing the wireless coupling distance between sensor 12 and reader 10. The connecting conductive leads may take any of a number of well-known forms, including wires, wire filaments, printed flex circuits, printed rigid circuits, feedthroughs, or rigid pins.

In the implantable embodiment, it may also be advantageous to design sensor 12 to be amenable to minimally invasive implant methods, such as catheter-based delivery. Additionally, it may be desirable for a portion of the implantable sensor to be radio-opaque or ultrasound-reflective, to aid implant and post-implant diagnostics.

Sensor 12 can be manufactured by a number of well-known technologies. Capacitive sensor 15 may be manufactured by microelectromechanical systems (MEMS) technology, lithographic techniques, or classic machining techniques. Inductor 13 may be a wirewound coil; an FR4, Teflon, Rogers, or other printed circuit board; a Low Temperature Cofired Ceramic (LTCC), greentape, or other ceramic printed circuit board; or any other inductor technology known to those in the art. Inductor 13 may be cored or non-cored, and may further utilize magnetic materials incorporated into one of the printed circuit board or ceramic technologies mentioned above. The inductor and capacitor may be packaged together as a multichip module (MCM).

Figure 6:
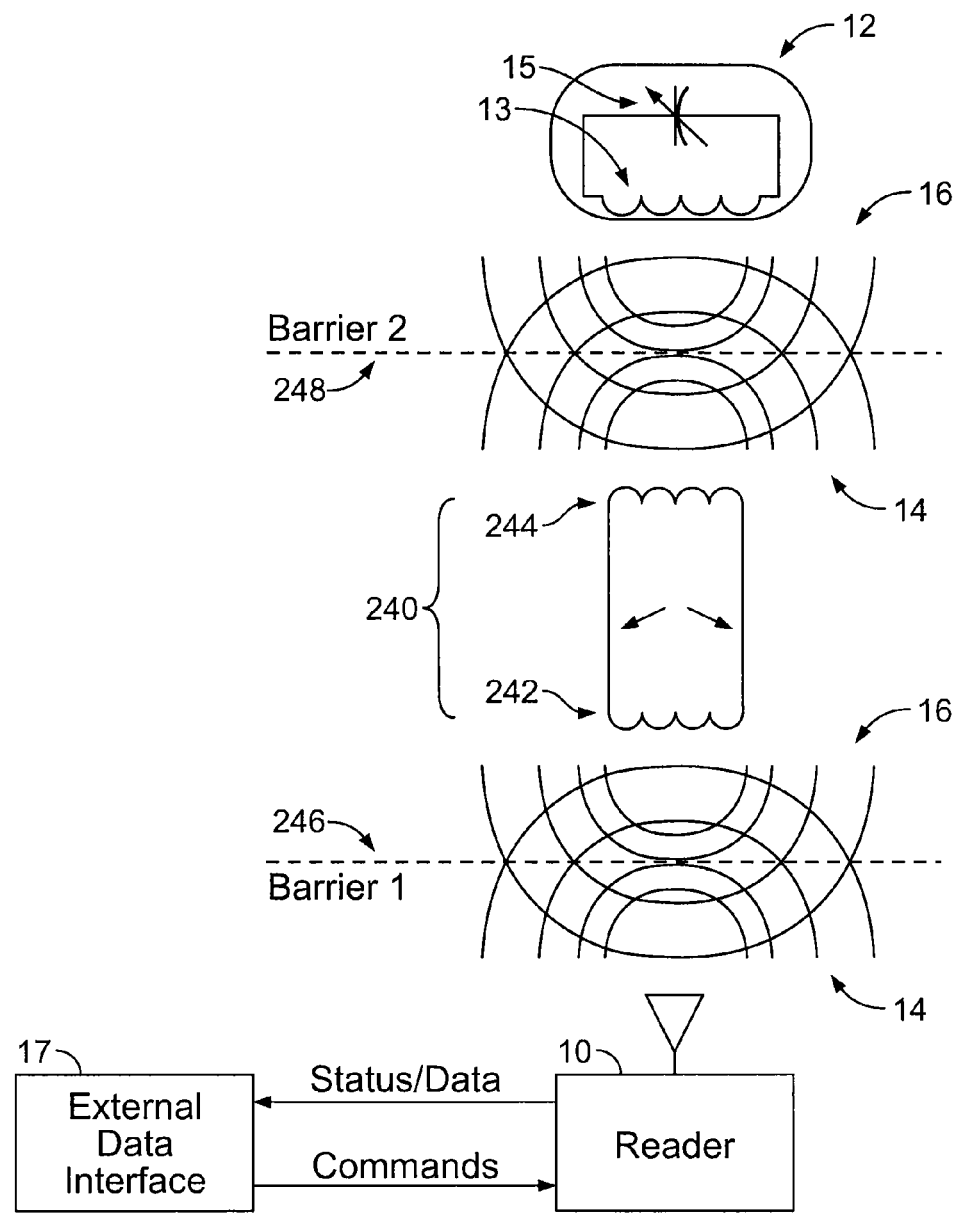
FIG. 6 is a block diagram of the passive wireless sensor system of FIG. 1, augmented by an intermediate antenna.

In another embodiment, the system of FIG. 1 may further comprise an intermediate antenna 240, as shown in FIG. 6. Intermediate antenna 240 comprises two antennas: reader-side antenna 242 and sensor-side antenna 244, which are connected together in series. The intermediate antenna 240 may improve signal coupling between reader 10 and sensor 12, and may be useful in cases where there are multiple barriers 246 and 248 between the reader 10 and sensor 12, which are not easily penetrated by conductive leads. As an example, for a sensor 12 implanted in a blood vessel, Barrier 2 (248) represents the blood vessel wall, and Barrier 1 (246) represents the skin surface. With the intermediate antenna 240 in place, signal coupling between reader 10 and sensor 12 is more efficient, as it takes place by conduction through leads rather than by radiation through whatever medium the system is in. Additionally, the antennas 242 and 244 can each be sized to match their corresponding antennas on sensor 12 and reader 10, further improving coupling efficiency. Finally, the sensor side antenna 244 can be aligned with precision across from sensor inductor 13, reducing errors due to misalignment between reader 10 and sensor 12 that might occur in the absence of the intermediate antenna 240. The intermediate antenna 240 can be made from flex circuits, wirewound coils, or other widely available means. Note too that the concept can be extended to applications where more than two barriers exist, by adding more intermediate antennas 240 for each pair of barriers.

In another embodiment, the sensor 12 in FIG. 1 may further comprise a second LC Tank circuit, with a separate inductor and capacitor, called the Reference Resonator. The Reference Resonator may be fabricated using the same materials, processes, and parts as the Sensing Resonator comprised of inductor 13 and capacitor 15, but with two key differences. First, the Reference Resonator's components are fixed in value and do not vary with the sensed parameter. Second, their fixed resonant frequency is designed to be outside the Operational Frequency Range 220 of the sensing resonator. The purpose of the Reference Resonator is to provide a background reading which can be used to correct the sensor reading acquired by the reader 12. Certain factors that lead to inaccuracy, such as reader distance, changes in the intervening medium, sensor orientation to the reader, aging of components, mechanical stress, electrical stress, outgassing, temperature, cell growth, blood clotting, etc, may affect the Reference Resonator in a manner similar to the sensing resonator. By understanding the relationship between Reference Resonator deviation from its fixed frequency and sensing resonator deviation from its nominal frequency, the reader can provide correction factors to the sensed frequency based on the Reference reading. In this embodiment, extra steps are introduced into FIG. 2 between steps 202 and 204, in which the reader 10 transmits an excitation pulse at the Reference Resonator's nominal resonant frequency, observes any deviation in Reference ring frequency, and calculates (or obtains from a lookup table) an appropriate correction factor for the forthcoming reading obtained in step 210. Alternatively, the reference reading can be taken after the sense reading. Although every change the Sensing Resonator undergoes may not affect the Reference Resonator in exactly the same way, this method of "self-calibration" may improve performance by eliminating or reducing some of the inaccuracies that are common to both resonators. These may be, for example, associated with distance, orientation, physiological reactions, changes in intervening tissue, and other long-term changes in sensor 12 behavior often referred to collectively as "sensor drift". Additionally, care must be taken in the frequency selection, and other design aspects of the Reference Resonator, to avoid coupling with the original sensing resonator, and common interaction with the reader.

Figure 7:
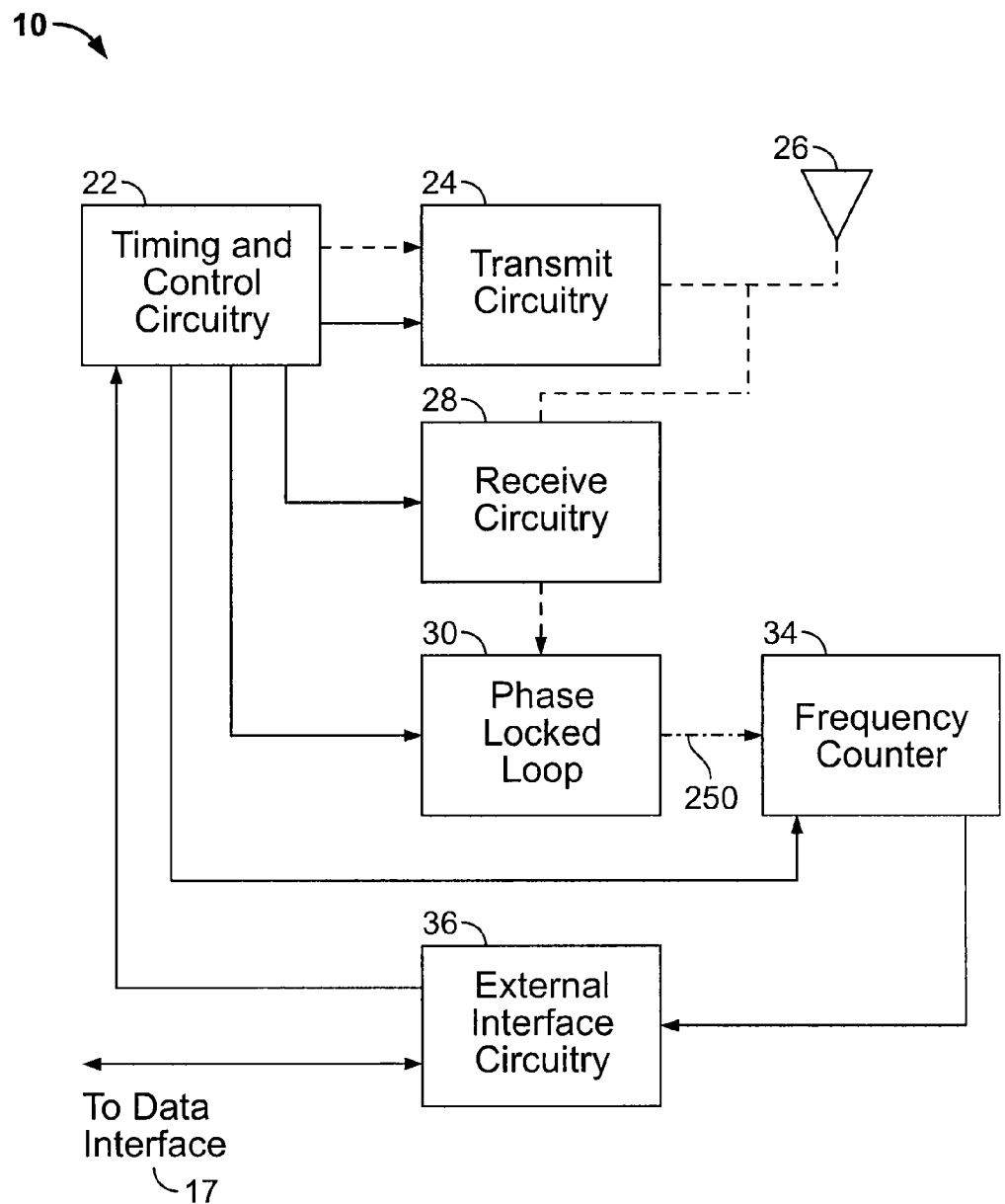
FIG. 7 is a top-level block diagram of the reader internal circuitry.

The reader 10 includes circuitry to send the excitation pulse 14, receive the ring signal 16, and process the ring signal 16. (FIG. 7.) For example, the reader 10 includes timing and control circuitry 22 to configure and activate the other circuits in the reader 10. The solid arrows to and from the timing and control circuitry 22 represent the control interfaces, such as digital or low-frequency signals. The timing and control circuitry 22 further generates an RF signal (illustrated as the broken line arrow) that is sent to transmit circuitry 24. The transmit circuitry 24 receives the RF signal and sends the excitation pulse 14 to antenna 26 to excite the sensor 12. The timing and control circuitry 22 may only provide the RF signal to the transmit circuitry 24 during the intervals when the excitation pulse is being transmitted to prevent leakage or coupling to other nodes in the system.

The reader 10 further includes an antenna 26 connected to the transmit circuitry 24 and the receive circuitry 28. The transmit circuitry 24 utilizes the antenna 26 for transmitting the excitation pulse 14, while the receive circuitry 28 utilizes the antenna 26 for receiving the ring signal 16. In an embodiment, the antenna 26 is connected to both the transmit circuitry 24 and the receive circuitry 28 at all times instead of being switched between transmit and receive. This shared antenna 26 design requires special consideration to prevent damage to the receive circuitry 28. Specifically, care must be taken not to overload the sensitive amplifier stages of the receive circuitry 28. Additionally, the reader 10 requires a fast transition between the extreme overdrive condition present while the transmit circuitry 24 is driving the antenna 26, and the low voltage condition present at the antenna 26 during the receive and amplify phases. For instance, the voltage at the antenna 26 may exceed 200 volts peak-to-peak during transmission of the excitation pulse, and may be single-digit millivolts, decaying rapidly to micro-volts, during reception immediately following the excitation pulse 14. While the reader 10 is described as having a shared antenna 26, it will be appreciated that the reader 10 may incorporate more than one antenna to separately perform the functions of transmitting the excitation pulse 14 and receiving the ring signal 16.

The reader 10 further includes a phase locked loop (PLL) 30 to receive and lock onto the ring signal 16. The receive circuitry 28 may amplify and condition the ring signal 16 before sending it to the PLL 30. The PLL 30 includes a voltage controlled oscillator ("VCO") 32 (not shown in FIG. 7) that may operate to lock a frequency within the range of sensor resonance frequencies when no signal is present, or may be chosen to prefer a frequency above or below the range of sensor resonance frequencies when no signal is present to enhance lock time when a sensor resonance frequency is received. In an embodiment, a PLL was chosen that performed better when the no-signal PLL lock frequency was slightly above the range of sensor resonant frequencies. VCO 32 generates an ac signal which is proportional to the ring signal frequency, called the count signal 250. The PLL 30 adjusts the divided-down count signal to match the ring signal 16 frequency, and sends the count signal 250 to a counter 34. The VCO 32 interfaces with frequency counter 34 which determines the count signal 250 frequency, and provides a digital signal representing that frequency to external interface circuitry 36 for transfer to the data interface 17. By operating the VCO 32 at a higher frequency than the ring signal 16, the time required to count and record the VCO 32 count signal 250 frequency may be significantly decreased.

Figure 8:
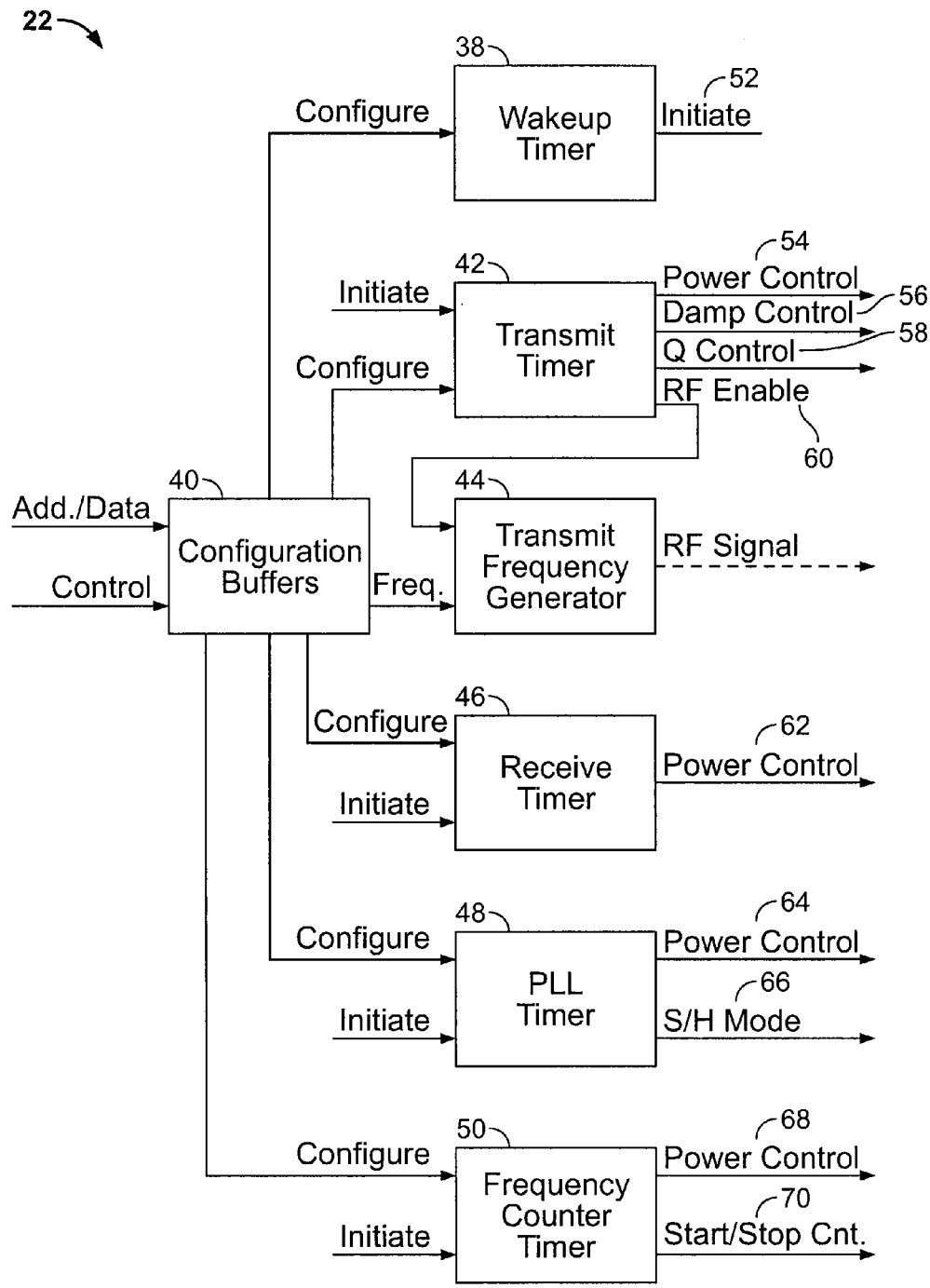
FIG. 8 is a block diagram of the timing and control portion of the reader circuitry.

Each component of the reader 10 is designed to operate efficiently and reduce power consumption. To that end, the reader 10 includes a reduced power functionality. The timing and control circuitry 22 controls the power status of each component by way of a wakeup timer 38 connected to each component. (FIG. 8.) In reduced power mode, some components may be completely powered down while other components may operate in a sleep mode, where power remains to maintain configuration but the circuit becomes static to minimize power consumption.

The timing and control circuitry 22 may place each component of the reader 10 in a sleep or powered-down mode when not in use. Additionally, the entire reader 10 may be placed in a low-power mode at the system level for periods of time specified by an external controller. The timing and control circuitry 22 may include a configuration buffer 40 that receives timing instructions from the external interface circuitry 36. The instructions establish the timing period before entering into reduced power mode, and other timing periods for the wakeup timer 38. Besides timing instructions from outside the reader 10, entry into/exit from reduced power mode may also be triggered by a threshold being exceeded for one of the on-board signals. The firmware of reader 10 may contain algorithms for deciding to enter/exit reduced power mode.

During a reading acquisition, the wakeup timer 38 may wake up each component of the reader 10 at the appropriate time to ensure that each component is in an operational state when needed. Specifically, the wakeup timer 38 may communicate with a transmit timer 42, a receive timer 46, a PLL timer 48, and a frequency counter timer 50 to wake up and control the respective components of the reader 10. Once initiated, each of these timers may control and power up the respective component. When configured, the wakeup timer 38 may delay for a specified interval, which may be zero seconds, before sending an initiate signal 52 to start the other timers. As illustrated in FIG. 8, the initiate signal 52 is not shown as a continuous line from the wakeup timer 38 to the respective timers in order to prevent line crossings and minimize confusion.

Once initiated, the transmit timer 42 establishes proper sequence and period to the power control 54, damp control 56, Q control 58, and RF enable 60 signals to properly sequence the transmit circuitry 24 and transmit frequency generator 44. The power control signal 54 controls the power status and sleep status of the transmit circuitry 24. The damp control signal 56 controls the activation of a damping circuit in the transmit circuitry 24 to quickly dissipate antenna 26 energy at the end of a transmission period. The Q control signal 58 controls a switching circuit in the transmit circuitry 24 to reduce the Q and modify the bandwidth of the antenna 26 during reception of the ring signal 16. The RF enable signal allows the transmit frequency generator 44 to send an RF signal to the transmit circuitry 24. In an embodiment, the transmit frequency generator 44 only provides the RF signal to the transmit circuitry 24 during periods where the transmit circuitry 24 is transmitting an excitation pulse 14.

The receive timer 46 is configured to establish proper sequence and period to the power control signal 62 to properly sequence the receive circuitry 28.

The PLL timer 48 establishes proper sequence and period to the power control 64 and S/H mode 66 signals to properly sequence the PLL 30. The power control signal 64 controls the power status and sleep status of the PLL 30. The S/H mode signal 66 controls a sample and hold circuit in the PLL 30, used to cause the PLL to lock onto the transmitted frequency then onto the ring signal 16 frequency, then hold the VCO 32 count signal 250 frequency at the locked frequency until that frequency is measured by the counter 34.

The frequency counter timer 50 establishes proper sequence and count interval to the power control 68 and start/stop count 70 signals to properly sequence the frequency counter 34. The power control signal 68 controls the power status and sleep status of the frequency counter 34. The start/stop count signal 70 controls the time that the frequency counter 34 begins and ends measuring the VCO 32 count signal 250 frequency.

Note that although FIG. 8 contains signals that share the same name, such as 'Initiate', 'Configure', and 'Power Control', each of these signals is unique to the circuit block it connects to. For example, power control signal 68 from Frequency Counter Timer block 50 is not the same signal as power control signal 64 from PLL Timer block 48, as described above.

The transmit circuitry 24 is configured to transmit the excitation pulse 14 to the sensor 12 by way of the antenna 26. (FIG. 7.) The excitation pulse 14 may be a fixed or rapidly varying frequency burst at or near the resonant frequency of the sensor 12. For example, the excitation pulse 14 may be a fixed frequency burst within several bandwidths of the sensor 12 resonant frequency. Alternatively, the excitation pulse 14 may be a fixed or rapidly varying frequency burst or sweep of a very short duration, at or near a frequency harmonically related to the sensor 12 resonant frequency. The excitation pulse 14 may also be an ultra-wide band pulse. This plurality of excitation pulse 14 approaches is possible because the ring signal 16 is received when the excitation pulse 14 transmissions have ceased. Therefore, excitation pulse 14 transmissions may be limited to frequency bands, amplitudes, and modulation schemes acceptable to regulatory government bodies. Radio frequency regulations may not apply to the sensor 12 as the sensor 12 is a purely passive device.

The excitation pulse 14 does not require significant transmission time because a single short transmission of energy results in a single and complete sample of the ring signal 16. Power consumption may be reduced by using a lower transmission duty cycle, thereby reducing the duty cycle of transmit, receive, counting, and digital processing circuitry. By reducing power consumption battery power becomes a much more viable option to power the reader 10.

The excitation pulse 14 may be configured to maximize several system parameters. For example, if a fixed frequency excitation pulse 14 is used, the frequency of the burst may be configured to maximize parameters such as maximum allowable transmit peak power, maximum freedom from in-band or near-band interference during the "receive" interval while the PLL is being locked to the ring signal 16, maximum worldwide acceptance of a particular frequency for reader transmissions for the desired sensor purpose, or other such criteria.

Figure 9:
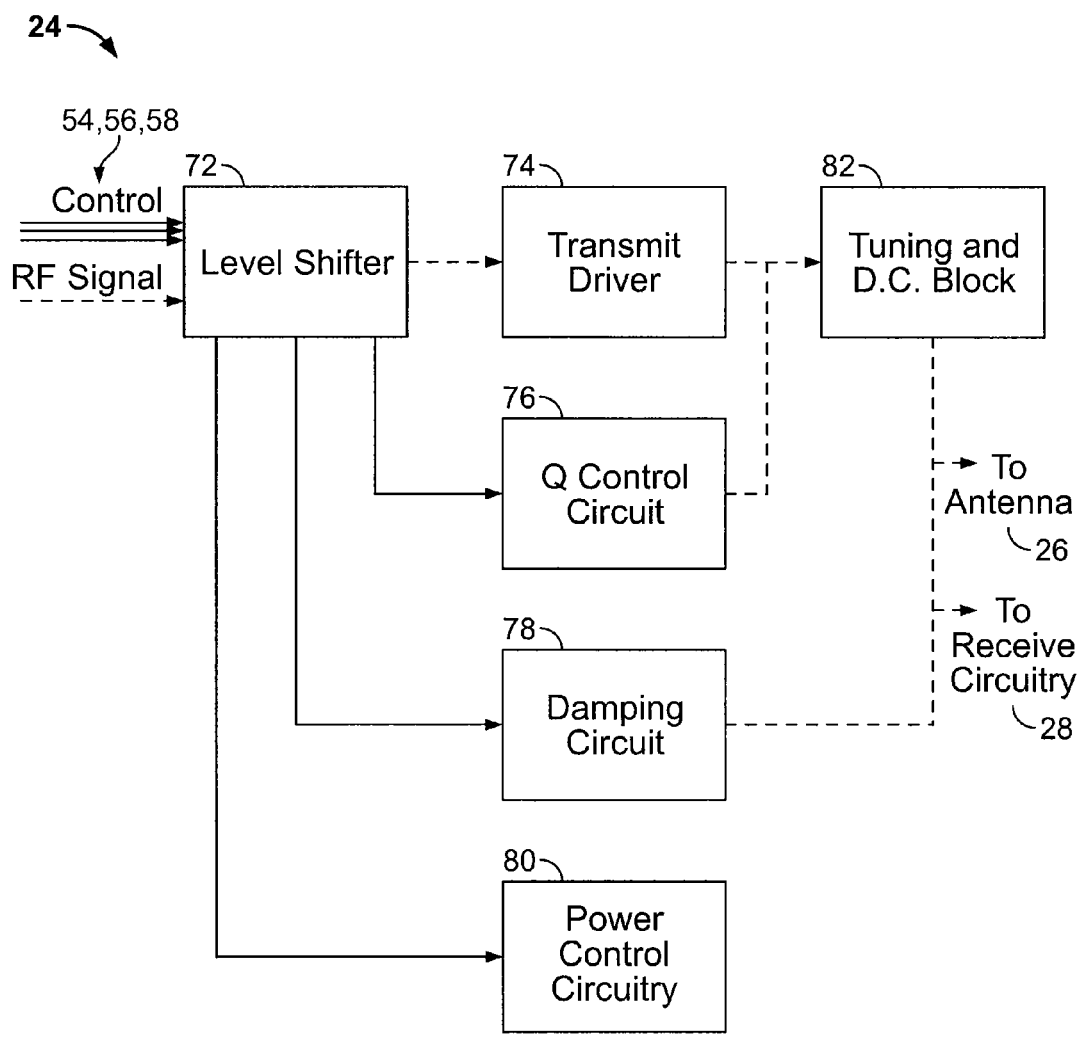
FIG. 9 is a block diagram of the transmit portion of the reader circuitry.

FIG. 9 illustrates the transmit circuitry 24. A level shifter 72 of the transmit circuitry 24 receives control signals 54, 56, 58 and the RF signal from the timing and control circuitry 22. The level shifter 72 buffers the inputs and converts control logic levels to circuit drive levels. A transmit driver 74 amplifies the RF signal to provide sufficient power to drive the antenna 26. The Q control circuit 76 is activated during receive to reduce the Q of the combined antenna 26 and tuning and D.C. block 82. A damping circuit 78 is briefly activated immediately at the end of transmission of the excitation pulse 14 to absorb energy in the antenna and allow the antenna to respond to the ring signal 16. The damping circuit 78 may provide a different Q factor to the antenna to improve reception of the ring signal 16. The power control circuitry 80 controls the power-on and sleep mode for components in the transmit circuitry 24. The tuning and D.C. block 82 adjusts tuning for the antenna 26 and prevents direct current from improperly biasing the damping circuit 78. The RF output or excitation pulse 14 from the transmit circuitry is routed to both the antenna 26 and the receive circuitry 28.

Figure 10:
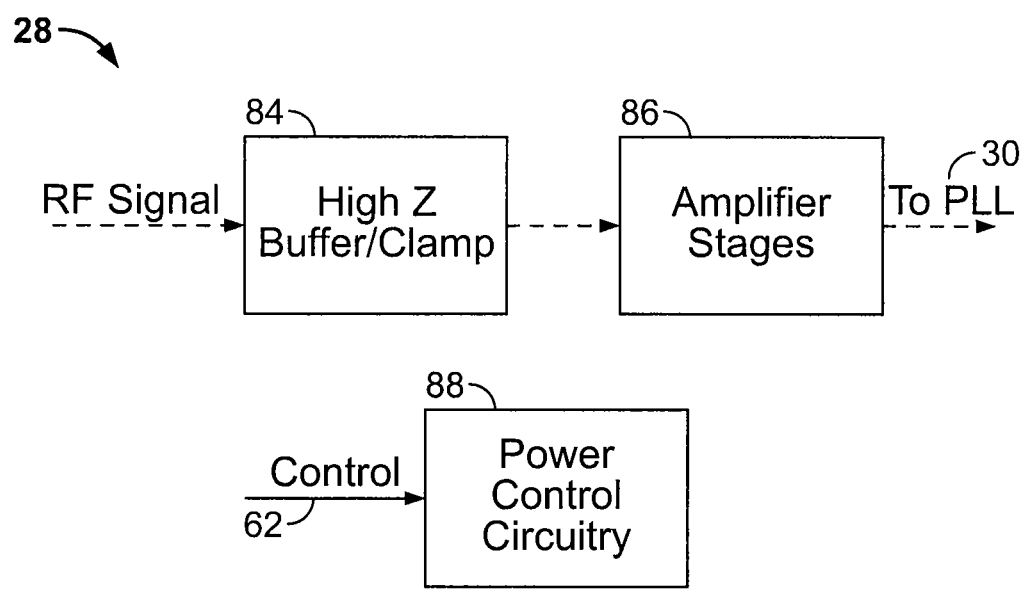
FIG. 10 is a block diagram of the receive portion of the reader circuitry.

Once the excitation pulse 14 is transmitted by the transmit circuitry 24, the receive circuitry 28 is configured to listen for the ring signal 16. With reference to FIG. 10, a high Z buffer/clamp 84 includes a high impedance ("high Z") input device that limits the effect of the receive circuitry 28 on the tuning performed by the tuning and D.C. block 82. The high Z buffer/clamp 84 further serves to protect the amplifier stages 86 from the extreme voltages present on the antenna 26 during transmission of the excitation pulse 14. Voltages at the antenna 26 may reach upwards of 200 volts peak-to-peak during transmission of the excitation pulse, requiring only approximately 60 pico-farads of capacitance to tune the antenna 26. In an embodiment, a 1 pico-farad capacitor is used as a high impedance input current limiting device on a 13.56 MHz transmit circuit. Low capacitance diode junctions that shunt over-voltage to the power supply and undervoltage to ground may be placed on the receiver side of the 1 pF capacitor, so that the capacitor limits current through the diodes as they protect the receiver amplifier from high voltages during transmission through the antenna 26.

The amplifier stages 86 amplify the ring signal 16 to a sufficient level to drive the PLL 30 input. Careful design of the amplifier stages 86 is required to achieve adequate transient response when the transmitted excitation pulse 14 signal is removed and damped, and the low level ring signal 16 is received. Common gate amplifier stages with low Q tuned reactive drain loads may be used to condition the high Z buffer/clamp 84 output, followed by several filters interspersed between high gain amplifier stages. The filters may be either resistor-capacitor ("RC") filters or inductor-capacitor ("LC") filters. In an embodiment, the filters may all be RC bandpass filters. Another common gate amplifier stage with low Q tuned reactive drain load may be used for final bandpass conditioning prior to feeding the signal to the PLL 30 input. This design enables all of these amplifier types to perform from extremely low signal input levels to extremely high signal input levels without signal distortion such as frequency doubling or halving due to stage saturation characteristics, as well as the excellent high input impedance achievable with the common-gate amplifier stages and the outstanding transient response characteristics of the RC filter interspersed between high gain amplifier stages. Special care must be taken in stage-to-stage power and signal isolation to prevent unwanted oscillations due to the extreme gain associated with the amplifier stages 86.

Power control circuitry 88 may apply and remove power to and from the amplifier stages 86 and the buffer in the high Z buffer/clamp 84 to reduce power consumption. It should be noted that the high Z buffer/clamp 84 is designed to provide full protection even with power removed as excess energy will merely power up the amplifier stages 86 until dissipated. The input impedance is high enough to limit excess energy to prevent overpowering the amplifier stages 86. In an embodiment, the receive circuitry 28 is active during the transmission of the excitation pulse 14 to decrease the time required for the PLL 30 to lock onto the ring signal 16.

Figure 11:
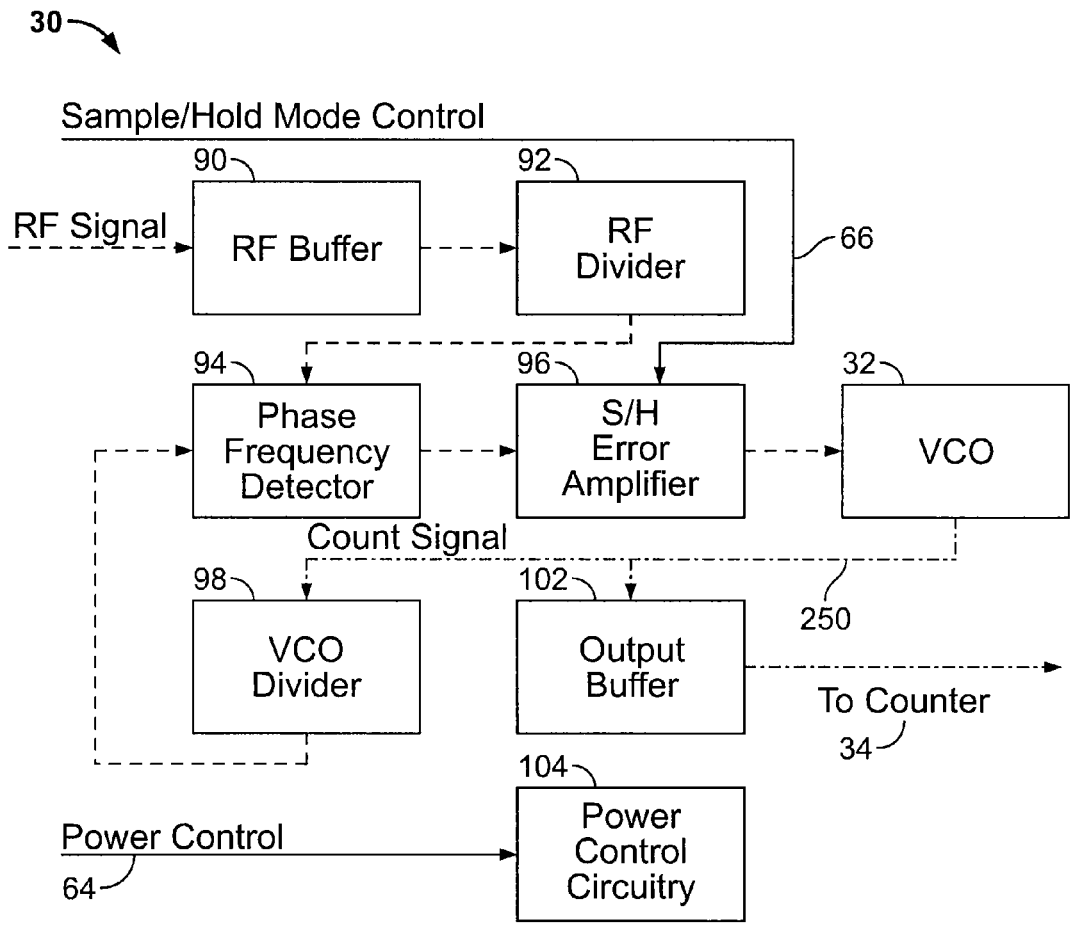
FIG. 11 is a block diagram of the phase locked loop portion of the reader circuitry.

The PLL 30 receives the amplified and conditioned ring signal 16 from the receive circuitry 28. With reference to FIGS. 10 and 11, the RF signal from the receive circuitry 28 amplifier stages 86 feeds an RF buffer 90 of the PLL 30. The RF buffer 90 may feed the RF signal to an optional RF divider 92 that divides the RF signal frequency by an integer value. (FIG. 11.) The RF divider 92 then feeds the RF signal to a first input of a phase frequency detector 94. The output of the frequency detector 94 feeds a sample-and-hold (S/H) error amplifier 96. The S/H error amplifier 96 controls the frequency of the VCO 32. The count signal 250 output by the VCO 32 feeds the VCO divider 98, which output in turn feeds a second input to the phase frequency detector 94. The PLL 30 may include an output buffer 102 to reduce loading of the VCO 32 while forwarding the count signal 250 frequency to the frequency counter 34. The VCO divider 98 allows the VCO 32 to operate at a frequency significantly higher than the ring frequency 16. As a result, the time required to count and record the VCO signal frequency may be significantly reduced. Moreover, the shorter count interval reduces VCO drift during counting and allows a higher sample rate.

The phase frequency detector 94 is configured to determine the frequency and phase error between the divided RF signal and the divided VCO signal. This is best accomplished by filtering and amplifying the signal that is fed to the S/H error amplifier 96. Further, the S/H feature may optimally forward the filtered and amplified signal to control the VCO 32. In this manner, a closed control loop is formed that causes the VCO 32 count signal 250 frequency to equal the ring signal 16 frequency times the VCO divider 98 integer divided by the RF divider 92 integer. The PLL 30 may include additional frequency dividers to optimize the circuit design and increase the potential VCO 32 frequency range.

The PLL timer 48 sends a S/H mode control signal 66 to the S/H error amplifier 96 of the PLL 30. The S/H mode control signal 66 may place the VCO 32 in a sample mode. In an embodiment, the VCO 32 is placed in sample mode for a predetermined length of time. In sample mode, the divided VCO count signal frequency is adjusted to match the ring signal 16 frequency, as described above. When the S/H mode control signal 66 is placed in the hold mode, the S/H error amplifier 96 will hold its output constant, causing the control voltage to the VCO 32 to be approximately constant over a length of time sufficient to determine the VCO 32 count signal 250 frequency.

The power control signal 64 from the PLL timer 48 to the power control circuitry 104 determines whether the PLL 30 is in a power on or a sleep/power-off mode to conserve electrical power. Depending on the specific PLL 30 that is used, a control and communication link (not shown) may be required to set the RF divider 92 integer, the VCO divider 98 integer, and the phase frequency detector 94 outputs and output configurations. The communications link may be specific to the particular PLL 30 used.

Figure 12:
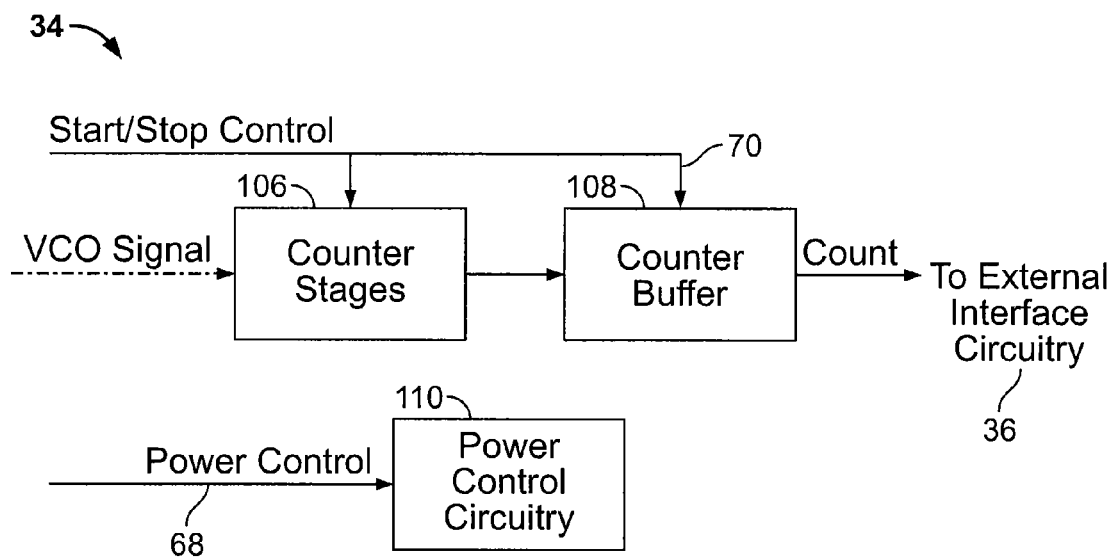
FIG. 12 is a block diagram of the frequency counter portion of the reader circuitry.

The frequency counter 34 includes counter stages 106, a counter buffer 108, and a power control circuitry 110 as shown in FIG. 12. The frequency counter timer 50 sends a start/stop control input 70 to the counter stages 106 and counter buffer 108. The frequency counter timer 50 also sends a power control input 68 to the power control circuitry 110. The counter stages 106 count the VCO signal frequency from the PLL 30 output buffer 102. The counter stages 106 start counting when the start/stop control commands start, and end when the start/stop control commands stop. When the start/stop control commands stop, the counter buffer 108 is loaded with the count value from the counter stages 106. The power control circuitry 110 controls the power-on and sleep modes for components in the frequency counter 34. The counter buffer 108 output may supply a count input to the external interface circuitry 36. The ring frequency 16, and subsequently the sensed parameter, may be determined from the frequency count.

In other embodiments, other methods for measuring the received and amplified frequency are possible. These may include direct counting of the ring signal, or various frequency-to-voltage conversion circuits known in the art.

In operation, the reader 10 sequences as follows. During periods of time when the sensor 12 is not being sampled, all components of the reader 10 are placed in reduced power mode. The wakeup timer 38 in the timing and control circuitry 22 is configured for a particular sample delay or sample interval. At the specified time, the wakeup timer 38 initiates a sample sequence. Specifically, the wakeup timer 38 powers up or wakes up each component of the reader at appropriate times to ensure each component is in an operational state when needed.

The external interface circuitry 36 is generally not required in the sampling sequence, except to receive the final data generated. Its entry into/exit from low power mode may be handled by internal or external controllers other than timing and control circuitry 22. The timing and control circuitry 22 provides the RF signal to the transmit circuitry 24 for a short period of time, such as approximately 20 microseconds. The RF signal from the timing and control circuitry 22 is then terminated and the transmit circuitry 24 is controlled to dampen the transmitted signal at the antenna 26 quickly. The transmit circuitry 24 is then placed in an appropriate mode to allow reception of the ring signal 16 at the antenna 26. In an embodiment, when the antenna 26 is configured to receive the ring signal 16, the antenna 26 damping is greater than the ring signal 16 damping.

During transmission of the excitation pulse 14, the receive circuitry 28 receives, conditions, and clamps the transmitted RF signal at the antenna 26. Once transmission of the excitation pulse 14 ceases and the antenna 26 is configured to receive the ring signal 16, the receive circuitry 28 transitions into a high-gain reception mode to receive the ring signal 16 from the antenna 26. The PLL 30 is in sample mode to allow the RF buffer 90 to receive the conditioned output of the receive circuitry 28. When the antenna 26 begins to receive the ring signal 16, the PLL 30 shifts from locking onto the transmitted excitation pulse 14 frequency, to locking onto the ring signal 16 frequency. After a time interval sufficient for the PLL 30 to lock onto the ring signal 16 frequency, the PLL 30 is shifted to hold mode to maintain VCO 32 count signal 250 frequency at ring signal 16 frequency. The time required to lock may be predetermined, or may be adaptive base on detected PLL locked conditions. After lock, the receive circuitry 28 and transmit circuitry 24 are powered down or placed in sleep mode as appropriate.

Once the PLL 30 is in hold mode, the timing and control circuitry 22 instructs the frequency counter 34 to conduct a controlled interval count of the VCO 32 count signal 250 frequency. Upon completion of the count, the PLL 30 components are powered down or placed in sleep mode as appropriate and the count value is transferred to the external interface circuitry 36. The frequency counter 34 components are then powered down or placed in sleep mode as appropriate, and subsequently the timing and control circuitry 22 components are powered down or placed in sleep mode as appropriate. If programmed for interval sampling, the timing and control circuitry 22 wakeup timer 38 counts until the next sample is due. Otherwise, the timing and control circuitry 22 awaits a wakeup command with any other needed instructions from the external interface circuitry 36. In burst sampling modes, the power up time needed for components to be ready may precede the power down time, in which case the components would remain powered up until completion of the sample burst.

Figure 13:
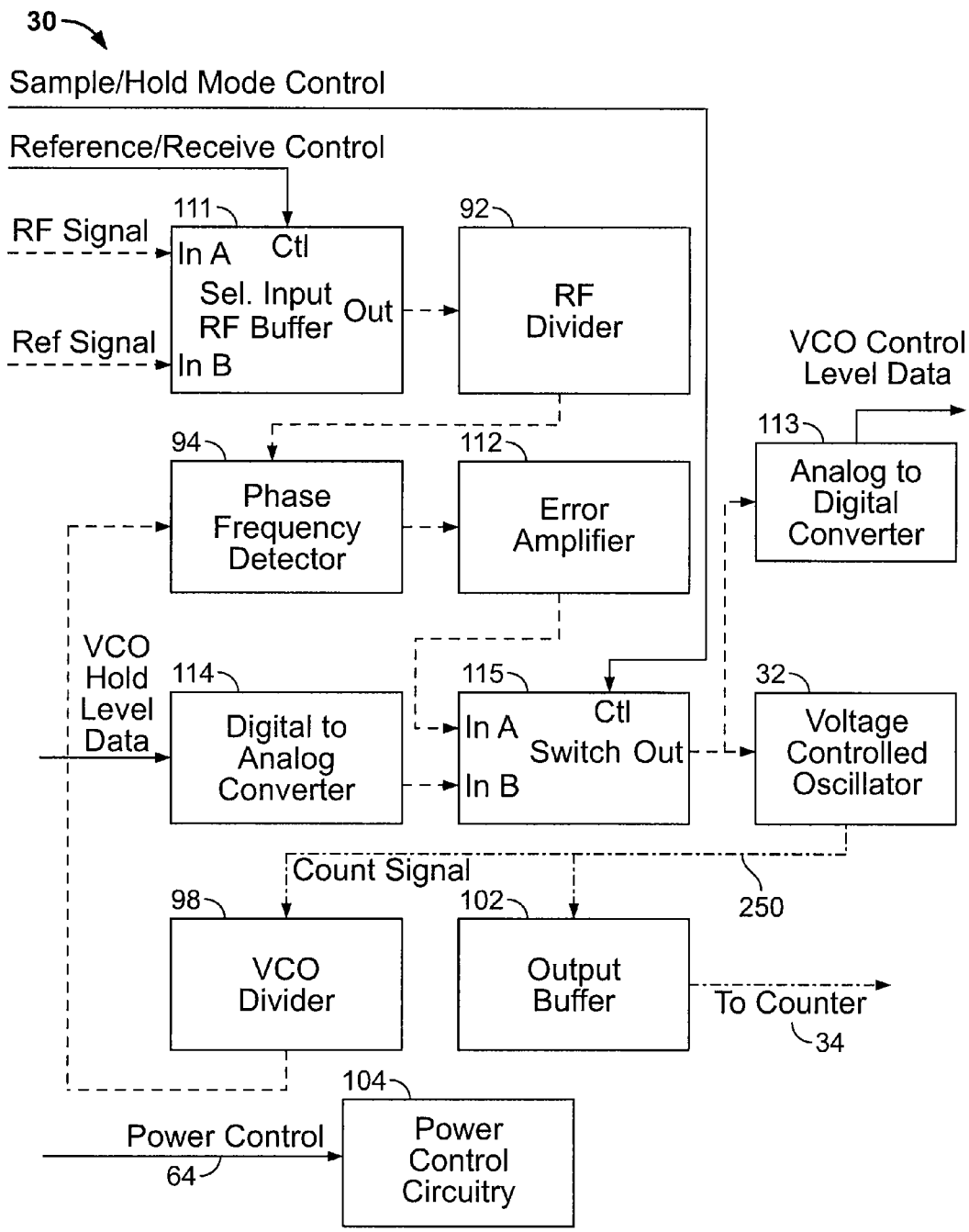
FIG. 13 is a block diagram of an alternate embodiment of the phase locked loop portion of the reader circuitry shown in FIG. 11, with a digital sampling timer and generation functionality for implementing the sample and hold.

An embodiment of the PLL circuit 30 in reader 10, shown in FIG. 13, includes several features that may be added to the PLL 30 to achieve alternate but equivalent functionality from the PLL 30 circuit described above. Some or all of the changes seen between FIG. 11 and FIG. 13 may be applied to enhance the operation of the FIG. 11 PLL 30. The selectable input RF Buffer 111 allows either the RF signal from amplifier stages 86, or a reference signal generated elsewhere in the reader 10, to be selected for input to RF Divider 92. The selection is determined by RF Buffer 111's reference/receive control input. The error amplifier 112 has been simplified and no longer provides directly the sample and hold capability previously described for the S/H error amplifier 96 from FIG. 11.

Circuit elements including an analog to digital (A/D) converter 113, a digital to analog (D/A) converter 114, and a switch 115, are illustrated in FIG. 13. These elements may be used to achieve the sample and hold feature. In the FIG. 13 configuration, a reference frequency signal "Ref Signal" may be selected as input to RF Buffer 111 during the reader 10 excitation pulse 14 transmission to the sensor 12, and the reference signal maintained until such time as the RF signal at In A of the selectable input RF buffer 111 becomes stable and available from the receive circuitry 28. This reference signal allows the PLL 30 to "pre-lock" on a stable reference signal, so reducing lock time when a ring signal becomes available from the receive circuitry 28. The output of the selectable input RF buffer is divided by any value equal to or larger than 1 by the RF divider 92, then the divided buffer signal is fed into the phase frequency detector 94. The output of the phase frequency detector 94 feeds an error amplifier 112 that provides the proper gain and frequency response needed to act as the control signal to the VCO 32 in the PLL 30. The output of the error amplifier 112 feeds input A of the switch 115. When selected to input A, the switch 115 passes the error amplifier 112 signal to both the VCO 32 and the A/D converter 113. The A/D converter 113 is then used to sample the control voltage to the VCO to determine the control voltage level at which the VCO 32 is locked at a frequency related to input A of the selectable input RF buffer 111. The A/D converter 113 signal may be used to measure the VCO 32 frequency indirectly as will be described later, and may be used to determine an appropriate setting for the D/A converter 114 such that the switch 115 can be set to input B to maintain the VCO 32 at the locked frequency input level for any period of time, achieving a digital sample and hold feature similar to that described for the S/H error amplifier 96 in FIG. 11.

Several slight modifications to the described operation of the FIG. 13 circuit may allow functionally equivalent results. One such modification is calibration of the A/D converter 113 voltage to specific receive circuitry 28 RF signal frequencies using input B of the selectable input RF buffer 111 fed with known frequencies. Once calibrated so that the relationship between signal input to RF buffer and the digital output of the A/D Converter 113 is well defined, the A/D Converter 113 output can be used to represent the ring signal 16 frequency. The A/D Converter 113 output becomes the PLL output. Operation in this manner will allow the A/D converter 113 to partially or completely supplant the functionality of the output buffer 102 and frequency counter 34.

Another modification in the described operation of the FIG. 13 circuit is to use the data from the A/D converter 113 for lock analysis of the PLL 30 to reduce lock time and improve lock frequency accuracy. This is possible because the output of the error amplifier 112 will converge upon the lock voltage value when the sensor 12 signal 16 is available at the output of the receive circuitry 28, then will diverge in a predictable manner when the sensor 12 signal 16 level decays past where lock can be maintained.

Another modification in the described operation of FIG. 13 circuit is to use the D/A converter 114 to generate specific voltages at the VCO 32 input, recording the A/D converter output at these specific voltages, and determining the frequency of the signal at the output of the output buffer 102, using the frequency counter 34. This allows calibration of the A/D converter for one or more frequencies using the frequency counter 34.

Minor modifications of FIG. 13 circuit that should be obvious to one of normal skill in electronic design include rearranging the location of the switch 115 and D/A converter 114 from the FIG. 13 shown location to between the phase frequency detector 94 and the error amplifier 112. This arrangement requires the additional step of calibration of the D/A converter 114 output through the error amplifier 112 to determine proper scaling to achieve a desired VCO 32 control voltage, done using either the A/D converter 113 or the frequency counter 34, or both. However, this arrangement allows the D/A converter 114 to be used for pre-lock instead of using the reference signal at input B of the selectable input RF buffer 111. This arrangement in combination with the A/D converter 113 calibration scheme previously described as allowing elimination of the output buffer 102 and the frequency counter 34, may allow for moderate reductions in power required to operate the reader 10 by shortening the time required to resolve the sensor 12 resonant frequency for each ring cycle. Another minor modification of the described embodiment is to distribute the system processing load in appropriate locations based on power limitations, computational complexity, time critical requirements, or other system-related priorities. Such a modification might lead a designer to place processing or analysis of data from the A/D converter 113, for the D/A converter 114, or the frequency counter 34 in any of the remote data system 18, the reader 10, or the external data interface 17.

Figure 14:
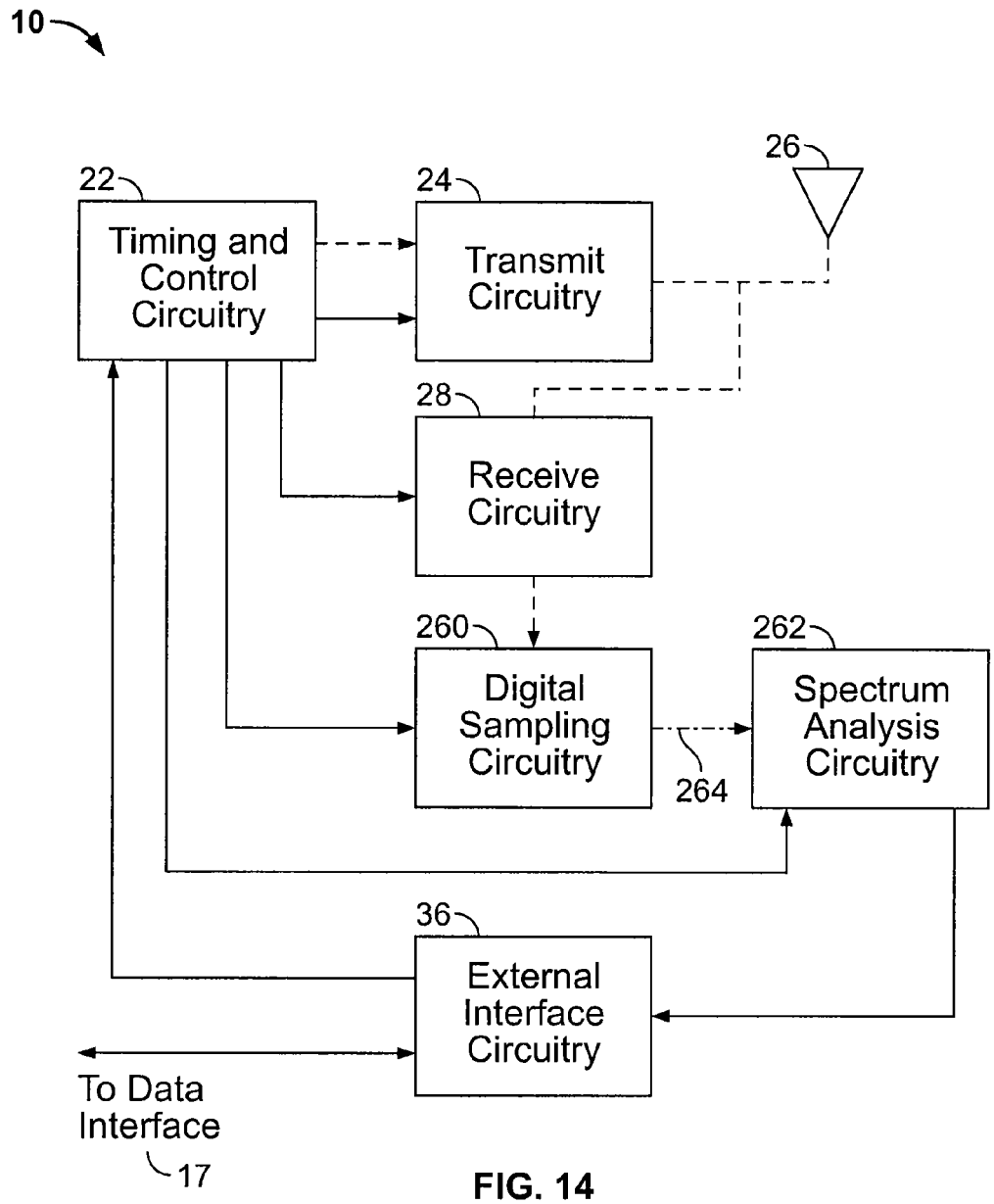
FIG. 14 is a block diagram depicting an alternate embodiment of the reader internal circuitry of FIG. 7, in which the PLL and Frequency Counter are replaced by Digital Sampling Circuitry and Spectrum Analysis Circuitry.

In yet another embodiment of reader 10 circuitry, digital spectrum analysis circuitry replaces PLL 30 and Frequency Counter 34 in FIG. 7, resulting in the modified block diagram shown in FIG. 14. Here Digital Sampling Circuitry 260 replaces PLL 30, and Spectrum Analysis Circuitry 262 replaces Frequency Counter 34. Analog Count signal 250 is likewise replaced by Digital Count Signal 264.

Functionally, digital sampling circuitry 260 extracts and digitizes information from the ring signal 16 during its short ring duration. The receive circuitry 28 may amplify and condition the ring signal 16 before sending it to the digital sampling circuitry 260. The digital sampling circuitry 260 may directly sample the radio frequency output of the receive circuitry 28 to obtain time-domain based data for further analysis.

In an embodiment, the reader 10 further contains spectrum analysis circuitry 262 for converting the time domain data output from the digital sampling circuitry 260 into frequency domain data, and for buffering the frequency domain data for forwarding to external interface circuitry 36. The spectrum analysis circuitry 262 may also include discrimination functionality to determine the ring frequency for the ring signal 16. As will be obvious to those skilled in the art, some or all of the spectrum analysis circuitry 262 functionality may be readily carried out by the reader 10 or by the remote data system 18, the major differences in the implementation being in the type and quantity of data sent via the external interface circuitry 36, and the needed processing power at the location where processing is done.

Figure 15:
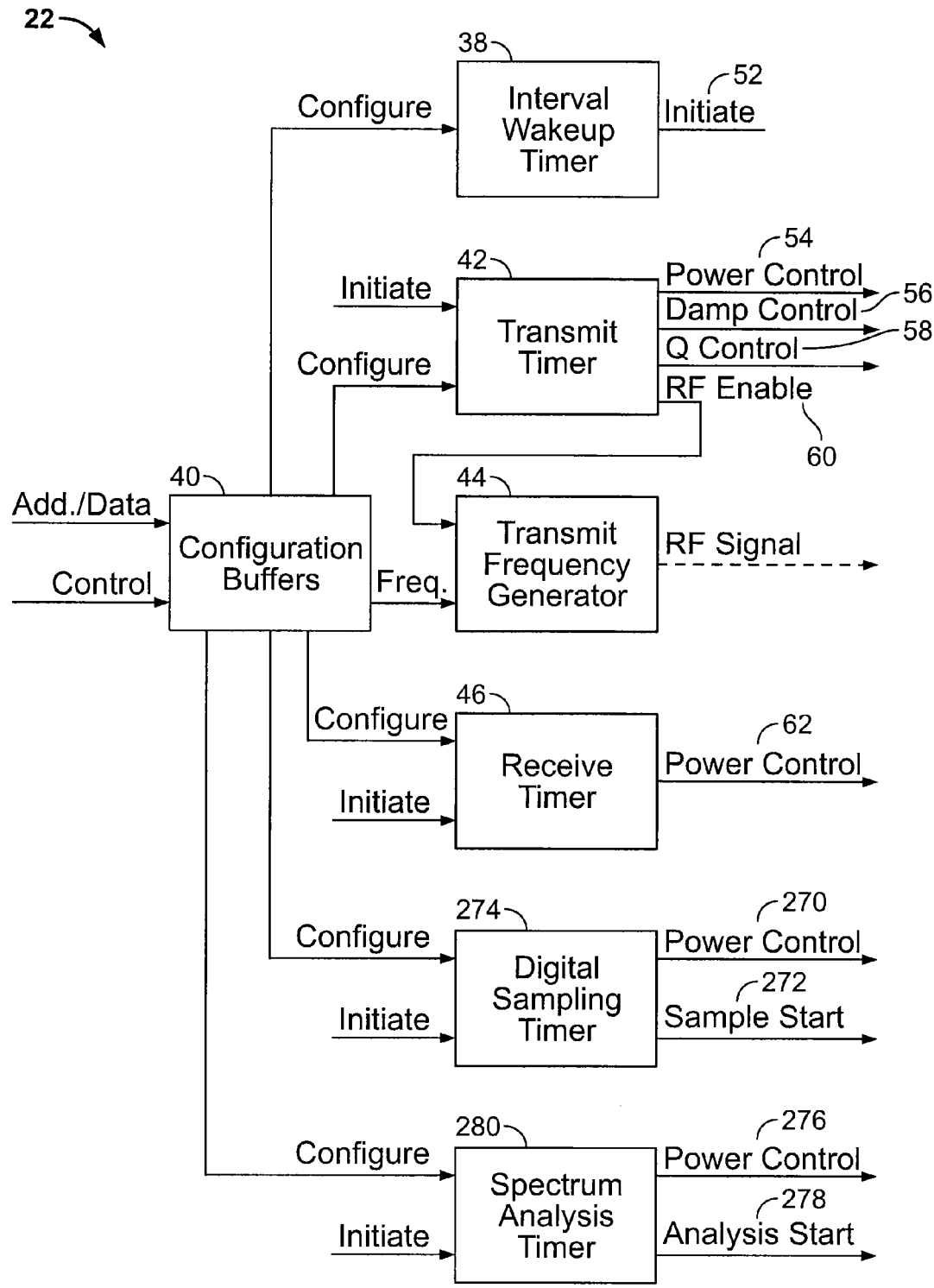
FIG. 15 is a block diagram depicting an alternate embodiment of the timing and control circuitry of FIG. 8, in which the PLL timer and Frequency Counter timer are replaced by a Digital Sampling timer and Spectrum Analysis timer, respectively.

Digital sampling circuitry 260 and spectrum analysis circuitry 262 are controlled by timing and control circuitry 22 in a manner similar to the PLL embodiment depicted in FIG. 8. The block diagram in FIG. 15 depicts an alternative embodiment of timing and control circuitry 22, adapted for controlling the alternative reader 10 circuitry shown in FIG. 14. PLL timer 48 in FIG. 8 is replaced by Digital Sampling timer 274 in FIG. 15. This timer establishes proper sequence and period to the power control 270 and sample start 272 signals to sequence the digital sampling circuitry 260. The power control signal 270 controls the power status and sleep status of the digital sampling circuitry 260. The sample start signal 272 causes the digital sampling circuitry 260 to gather an appropriate number of samples in a burst sample mode for sending to the spectrum analysis circuitry 262.

Likewise, frequency counter timer 50 in FIG. 8 is replaced by spectrum analysis timer 280 in FIG. 15. The spectrum analysis timer 280 establishes proper sequence and timing to the power control 276 and analysis start 278 signals, to sequence the spectrum analysis circuitry 262. The power control signal 276 controls the power status and sleep status of the spectrum analysis circuitry 262. The analysis start signal 278 controls the time that the spectrum analysis circuitry 262 begins evaluating the sample burst 264 provided by the digital sampling circuitry 260.

Receive circuitry 28 in the alternative embodiment of FIG. 14 is functionally and architecturally equivalent to receive circuitry 28 in the PLL-based embodiment of FIGS. 7 and 10, the only difference being the output signal from amplifier stages 86 feeds analog-to-digital converter 290 at the input of digital sampling circuitry 260, rather than PLL 30.

Figure 16:
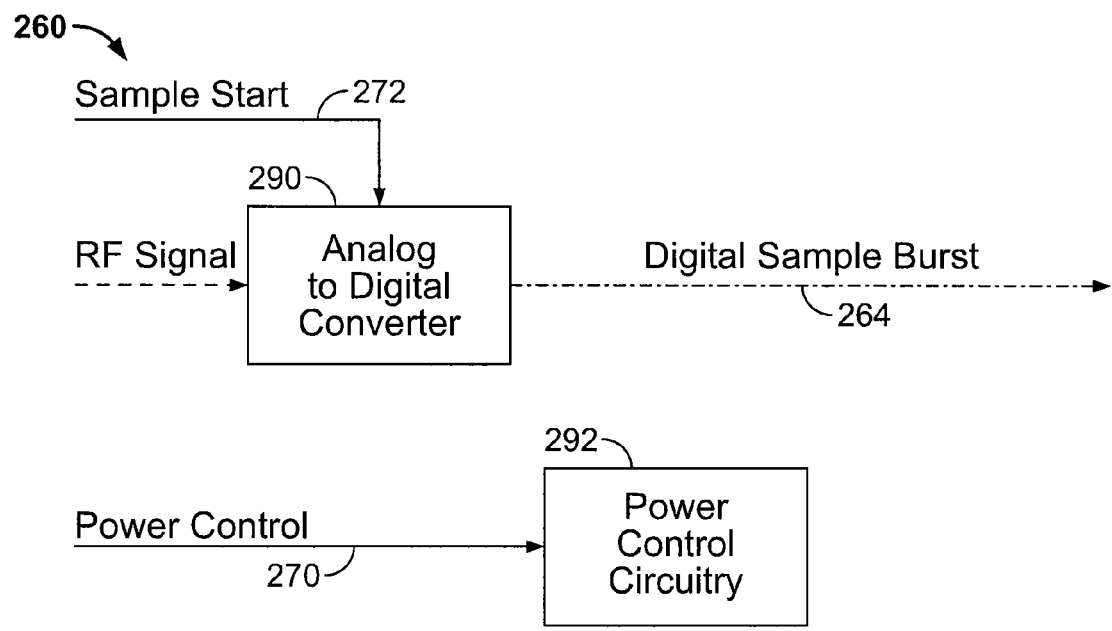
FIG. 16 is a block diagram of the internal architecture of the Digital Sampling Circuitry block of FIG. 14.

FIG. 16 is a block diagram depicting an embodiment of digital sampling circuitry 260. The RF signal from the receive circuitry 28 amplifier stages 86 feeds the input to the analog to digital converter (ADC) 290 of the digital sampling circuit 260. The ADC 290 converts the RF signal into a set of time-related samples taken at close enough intervals and with sufficient sample quantity to allow the spectrum analysis circuitry 262 to achieve its required frequency accuracy. This set of time-related samples will be referred to here as a digital sample burst 264.

Figure 17:
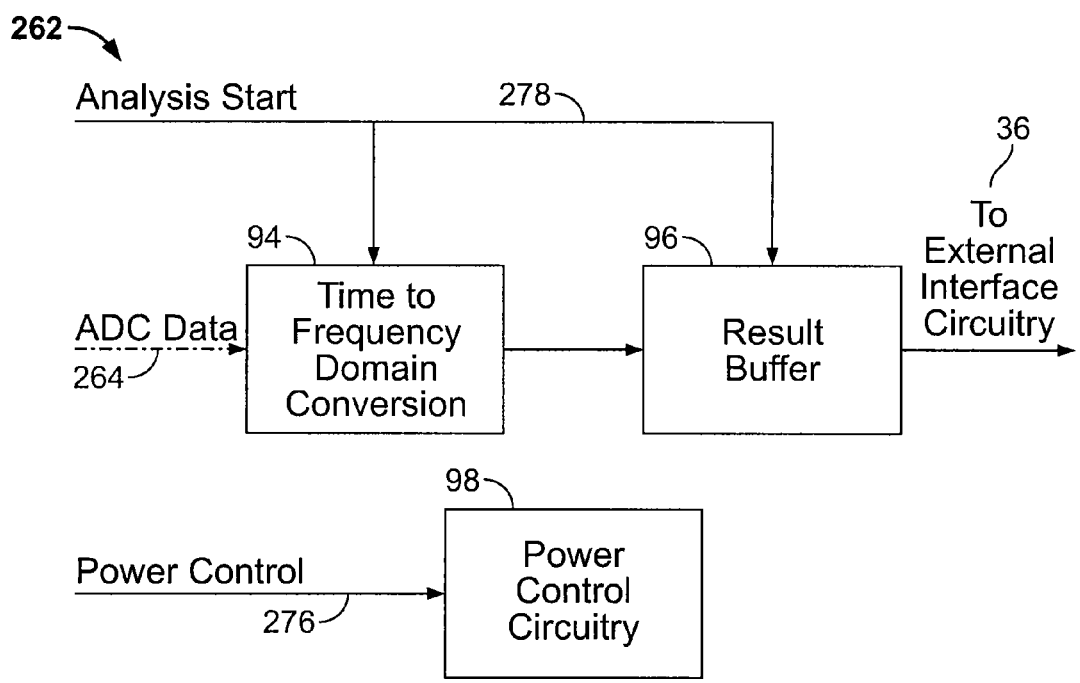
FIG. 17 is a block diagram of the internal architecture of the Spectrum Analysis Circuitry block of FIG. 14.

The digital sample burst 264 output from the ADC 290 is fed into the spectrum analysis circuitry 262 time to frequency domain conversion circuit 94, shown in FIG. 17. The internal workings of the frequency domain conversion 94 are not here specified as this conversion may be any of several means which might include fast or discrete Fourier transform, discrete or continuous wavelet transform, any of the several Laplace transforms, any of the several Z-transforms, or other conversion algorithms known in the art. The internal workings of the frequency domain conversion 94 may be implemented in hardware or software or any combination of both to achieve the desired conversion. Since the output of the frequency domain conversion 94 will be generated at the sampling interval, and may contain multiple values for transfer to the external data interface 17, a result buffer 96 is shown in the spectrum analysis circuitry 262 to hold these values until they can be transferred to the external data interface 17.

In this digital spectrum analysis embodiment, the reader 10 operating sequence is similar to that described in "Reader Operational Sequence" above, except that the digital sampling circuitry 260 and spectrum analysis circuitry 262 perform the functions related to determination of the ring signal 16 frequency. When the antenna 26 begins to receive the ring signal 16, the digital sampling circuit 260 rapidly samples for a predetermined or computed period to obtain a digital sample burst 264. After completion of the digital sample burst 264, the receive circuitry 28 and digital sampling circuit 260 are powered down or placed in sleep mode as appropriate. The spectrum analysis circuit 262 converts the digital sample burst 264 data to frequency domain and places the result into the result buffer 96, then is shifted to a low power mode. Subsequently, the timing and control circuitry 22 components are powered down or placed in sleep mode as appropriate. If programmed for interval sampling, the timing and control circuitry 22 wakeup timer 38 counts until the next sample is due. Otherwise, the timing and control circuitry 22 awaits a wakeup command with any other needed instructions from the external interface circuitry 36. The sample data in the result buffer 96 is kept available to the external interface circuitry 36 for transfer to the remote data system 18 as controlled by the communications interface.

It will be obvious to anyone skilled in the art that numerous minor modifications may be made to the described digital spectral analysis embodiment to achieve functionally equivalent results. One such modification is the use of zero-padding of the ADC data, as is common practice with time domain to frequency domain conversions where signal burst data is evaluated. Another such modification is moving the physical location of the spectrum analysis circuit 262 from the reader 10 to the remote data system 18, with ADC 90 data transmitted in time-domain form from the reader 10 to the remote data system 18. Yet another such modification is frequency converting the ring signal 16 at some point in the reader 10 by frequency multiplication, division, sum, or difference circuitry, changing the ring signal 16 to an intermediate frequency signal for any of numerous reasons related to frequency selectivity, bandwidth, sampling time, etc. Yet another such modification is the use of digital signal processing techniques to filter, shape, analyze, compare with other data, or otherwise process and evaluate the frequency domain or the time domain data.

Likewise, those skilled in the art will readily observe that combinations of the various frequency determination methods disclosed herein are possible and may be advantageous in different applications. For example, an analog sample and hold circuit may be used in combination with digital spectral analysis, in order to hold the ring signal 16 long enough to obtain an adequate sample for digitizing.

In another embodiment, a standard RFID tag, of a type known to those in the art, may be incorporated with sensor 12. Such tag may have a separate antenna, and operate at a frequency outside Sensor Operational Range 220. It can be encoded with configuration information on the sensor 12.

The embodiment of the invention has been described above and, obviously, modifications and alternations will occur to others upon reading and understanding this specification. The claims as follows are intended to include all modifications and alterations insofar as they are within the scope of the claims or the equivalent thereof.

We claim:

1. A method of obtaining a measurement from a remote location, the method comprising:
    transmitting at least one excitation pulse at a fixed frequency to a wireless sensor;
    receiving at least one signal from said wireless sensor in response to said at least one excitation pulse;
    sampling said received signal; and
    holding the frequency of said received signal constant by a reader for a length of time sufficient to ascertain said received signal, wherein said wireless sensor is configured to change its resonant frequency in proportion to at least one sensed parameter.

2. The method of claim 1 further comprising transmitting a plurality of said excitation pulses at said fixed frequency, receiving a plurality of said signals and ascertaining the frequencies of said signals.

3. The method of claim 2 wherein said plurality of ascertained frequencies are averaged.

4. The method of claim 1 wherein said excitation pulse is a radio frequency (RF) signal.

5. The method of claim 4 wherein the frequency of said excitation pulse is approximately 13.56 MHz.

6. The method of claim 1 further comprising the step of incorporating said wireless sensor with a device that provides a separate function.

7. The method of claim 1 wherein said signal is a ring signal.

8. The method of claim 1 further comprising the steps of:
    transmitting at least one reference excitation pulse at a reference frequency, different from said fixed frequency;
    receiving at least one reference response signal from a fixed reference resonator incorporated with said wireless sensor in response to said at least one reference excitation pulse;
    sampling and holding said reference response signal;
    ascertaining the frequency of said reference response signal; and
    improving the correlation of said received signal to said at least one sensed parameter based on said ascertained frequency.

9. A system for obtaining a measurement from a remote location, said system comprising:
    a wireless sensor configured to change its resonant frequency in proportion to at least one sensed parameter; and
    a reader configured to transmit at least one excitation pulse at a fixed frequency to said wireless sensor, to receive at least one signal from said wireless sensor in response to said excitation pulse, to sample said received signal, and to hold the frequency of said received signal constant for a length of time sufficient to ascertain the frequency of said received signal.

10. The system of claim 9 wherein said wireless sensor comprises at least one capacitor and at least one inductor, and wherein said at least one inductor varies with said at least one sensed parameter.

11. The system of claim 9 wherein said wireless sensor comprises at least one capacitor and at least one inductor, and wherein said at least one capacitor varies with said at least one sensed parameter.

12. The system of claim 9 wherein said wireless sensor is incorporated with a device that provides a separate function.

13. The system of claim 9, further comprising an intermediate antenna, located between said reader and said wireless sensor.

14. The system of claim 13, wherein said intermediate antenna comprises two antennas, connected together by conductive leads.

15. The system of claim 14, wherein the first of said two antennas is located and designed for optimum communication with said reader.

16. The system of claim 14, wherein the second of said two antennas is located and designed for optimum communication with said wireless sensor.

17. The system of claim 9, wherein said at least one excitation pulse is at least one of:
    a burst containing a frequency within a bandwidth of plus or minus twenty percent of the frequency of said received signal;
    a burst containing a frequency within a bandwidth of plus or minus twenty percent of a sub-harmonic frequency of said received signal;
    an ultra-wide-band pulse having a pulse width less than twice said signal period and a spectral content of not less than one third of the frequency of said received signal; and
    a burst consisting of not less than ten cycles and not more than ten thousand cycles at a frequency not less than eight tenths the frequency of said received signal and not more than twelve tenths the frequency of said signal.

18. The system of claim 9 wherein said signal is a ring signal.

19. The system of claim 9 wherein said reader is a handheld device.

20. The system of claim 9 wherein said reader is powered by a battery.

21. The system of claim 9 wherein said wireless sensor further comprises an additional resonant circuit having a resonant frequency different from the fixed resonant frequency of the wireless sensor.

22. The system of claim 21, wherein said reader is further configured to transmit a second excitation pulse at said fixed frequency of said additional resonant circuit, and to receive a response from said additional resonant circuit.

23. The system of claim 22, wherein said reader is further configured to ascertain the frequency of said response from said additional resonant circuit for the purpose of calibrating said at least one received signal.

24. A wireless sensor reader comprising:
    a transmit circuit configured to generate at least one excitation pulse to cause a wireless sensor to emit at least one response signal;
    at least one antenna configured to transmit said excitation pulse and receive said response signal;
    a phase-locked loop circuit configured to receive said response signal from said at least one antenna, said phase-locked loop circuit including a voltage-controlled oscillator configured to generate a count signal at a frequency related to said response signal frequency;

a first circuitry configured to sample a control voltage input of said voltage-controlled oscillator;

a second circuitry configured to generate a control voltage signal for input to said voltage-controlled oscillator;

wherein said phase-locked loop circuit is capable of being placed in a sample mode to receive said response signal and adjust the frequency of said count signal based on the frequency of said response signal;

wherein said phase-locked loop circuit is further capable of being placed in a hold mode to hold the frequency of said count signal constant to extend the duration of said count signal for a length of time sufficient to determine the frequency of said count signal; and wherein said first circuitry and said second circuitry reconfigure said phase-locked loop circuit between said sample mode and said hold mode.

25. The wireless sensor reader of claim 24, wherein said first circuitry further comprises analog-to-digital conversion circuitry.

26. The wireless sensor reader of claim 25, wherein the value obtained from said analog-to-digital conversion circuitry is used to configure said phase-locked loop circuit to said hold mode.

27. The wireless sensor reader of claim 25, wherein the value obtained from said analog-to-digital conversion circuitry is used to determine a point at which to evaluate said count signal frequency.

28. The wireless sensor reader of claim 24, wherein said second circuitry further comprises digital-to-analog conversion circuitry.

29. The wireless sensor reader of claim 24, further comprising a switch for selecting the input to said voltage-controlled oscillator from between said generated control voltage signal and the output of the phase detector of said phase-locked loop.

30. The wireless sensor reader of claim 24, wherein said reader is configured to hold said voltage-controlled oscillator frequency at a generated fixed frequency during at least a portion of the time when said response signal is not present.

31. The wireless sensor reader of claim 24, wherein said control voltage input of said voltage-controlled oscillator that corresponds to said count signal frequency is output directly from said phase-locked loop circuit.

32. The wireless sensor reader of claim 24, wherein said phase-locked loop circuit further includes circuitry for internal calibration.

33. The wireless sensor reader of claim 32, wherein said calibration circuitry enables said control voltage input of said voltage-controlled oscillator to be correlated with said response signal frequency.

34. The wireless sensor reader of claim 33, wherein said calibration circuitry enables the introduction of a reference signal into said phase-locked loop in place of said response signal.

35. The wireless sensor reader of claim 33, wherein said calibration circuitry enables the introduction of a reference voltage into said voltage controlled oscillator in place of said control voltage input, and the evaluation of said voltage-controlled oscillator output frequency.

36. The wireless sensor reader of claim 24 wherein said response signal is a ring signal.

37. The wireless sensor reader of claim 24 wherein said excitation pulse has a fixed frequency.

38. The wireless sensor reader of claim 24 wherein said transmit circuit is further configured to generate at least one excitation pulse at a fixed reference frequency, to cause a reference resonator on said wireless sensor to emit a reference response signal.

39. The wireless sensor reader of claim 38 wherein said wireless sensor reader is further configured to measure said reference response signal frequency and utilizes it to improve the accuracy of the reading obtained from said wireless sensor.

40. A method of reading a wireless sensor comprising:

transmitting at least one excitation pulse to a wireless sensor;

receiving at least one response signal from said wireless sensor in response to said excitation pulse;

amplifying said response signal; locking an oscillator to a frequency harmonically related to said response signal; digitally sampling the control voltage of said oscillator; regenerating said digitally sampled control voltage of said oscillator; and switching said regenerated voltage to control said oscillator, and holding said regenerated voltage in control of said oscillator constant for a length of time sufficient to determine the frequency of said oscillator.

41. The method of claim 40, including the additional step of controlling said oscillator with a reference voltage during at least a portion of the time when said response signal is not present.

42. The method of claim 40, including the additional step of supplying a reference signal for frequency locking in place of said response signal, during at least a portion of the time when said response signal is not present.

43. The method of claim 40 wherein said response signal is a ring signal.

* * * * *

UNITED STATES PATENT AND TRADEMARK OFFICE
CERTIFICATE OF CORRECTION

PATENT NO. : 8,493,187 B2
APPLICATION NO. : 12/727306
DATED : July 23, 2013
INVENTOR(S) : Harry D. Rowland et al.

It is certified that error appears in the above-identified patent and that said Letters Patent is hereby corrected as shown below:

Title Page, (75) delete "Roger Dwight Walking" and insert --Roger Dwight Watkins--

Signed and Sealed this
Fifteenth Day of October, 2013

Teresa Stanek Rea
*Deputy Director of the United States Patent and Trademark Office*